(12) United States Patent
Mandell et al.

(10) Patent No.: US 11,976,322 B2
(45) Date of Patent: May 7, 2024

(54) TUNING AND CALIBRATION FEATURES OF SEQUENCE-DETECTION SYSTEM

(71) Applicant: Illumina, Inc., San Diego, CA (US)

(72) Inventors: Jeffrey G. Mandell, San Diego, CA (US); Kevin L. Gunderson, San Diego, CA (US); Michael Gregory Keehan, San Diego, CA (US); Erin Christine Garcia, San Diego, CA (US)

(73) Assignee: ILLUMINA, INC., San Diego, CA (US)

( * ) Notice: Subject to any disclaimer, the term of this patent is extended or adjusted under 35 U.S.C. 154(b) by 505 days.

(21) Appl. No.: 16/623,634

(22) PCT Filed: Sep. 14, 2018

(86) PCT No.: PCT/US2018/051191
§ 371 (c)(1),
(2) Date: Dec. 18, 2019

(87) PCT Pub. No.: WO2019/055856
PCT Pub. Date: Mar. 21, 2019

(65) Prior Publication Data
US 2020/0123603 A1    Apr. 23, 2020

Related U.S. Application Data

(60) Provisional application No. 62/559,251, filed on Sep. 15, 2017.

(51) Int. Cl.
*C12Q 1/6869* (2018.01)
*B01L 3/00* (2006.01)
*G01N 27/447* (2006.01)

(52) U.S. Cl.
CPC ...... *C12Q 1/6869* (2013.01); *B01L 3/502707* (2013.01); *B01L 3/502715* (2013.01); *G01N 27/44791* (2013.01)

(58) Field of Classification Search
None
See application file for complete search history.

(56) References Cited

U.S. PATENT DOCUMENTS

| 7,371,532 B2 | 5/2008 | Mamine et al. |
| 8,652,779 B2 | 2/2014 | Turner et al. |

(Continued)

FOREIGN PATENT DOCUMENTS

| JP | 2010-26067 A1 | 4/2010 |
| JP | 2017-503473 A | 2/2017 |

(Continued)

OTHER PUBLICATIONS

Tanaka, Mami, et al., "A Wearable Braille Sensor System With a Post Processing," IEEE, vol. 12, No. 4, Aug. 2007.

(Continued)

*Primary Examiner* — Matthew D Krcha
(74) *Attorney, Agent, or Firm* — MARSHALL, GERSTEIN & BORUN LLP

(57) ABSTRACT

The current document discusses electromechanical sequence detectors that transduce changes in the shape of a shape-change sensor component into an electrical signal from which one or more derived values are generated. In a disclosed implementation, the sequence-detection system comprises a mechanical-change sensor that changes shape when specifically interacting with entities within a target, a shape-to-signal-transduction component that transduces changes in the shape of the mechanical-change sensor into an electrical signal, an analysis subsystem that determines the types of entities within the target using the electrical signal, and a control subsystem that continuously monitors operational characteristics of the sequence-detection system and adjusts sequence-detection system operational parameters.

12 Claims, 39 Drawing Sheets

(56) References Cited

U.S. PATENT DOCUMENTS

| | | | |
|---|---|---|---|
| 8,943,611 B2 | 1/2015 | Cannara et al. | |
| 9,494,554 B2 | 11/2016 | Davis et al. | |
| 2005/0026163 A1 | 2/2005 | Sundararajan et al. | |
| 2011/0020806 A1* | 1/2011 | Pourmand | C12Q 1/6869 435/6.1 |
| 2014/0147833 A1 | 5/2014 | Astier et al. | |
| 2015/0344945 A1* | 12/2015 | Mandell | G01N 27/44743 204/453 |
| 2017/0042038 A1 | 2/2017 | Hamaguchi et al. | |
| 2019/0002968 A1* | 1/2019 | Bergmann | C12Q 1/6869 |

FOREIGN PATENT DOCUMENTS

| | | |
|---|---|---|
| JP | 2017-503473 A1 | 2/2017 |
| WO | 2013033647 A3 | 3/2013 |
| WO | 2016/100635 A1 | 6/2016 |
| WO | 2016196755 A | 12/2016 |
| WO | 2017027518 A1 | 2/2017 |
| WO | WO-2017/027518 A1 | 2/2017 |
| WO | 2017/042038 A1 | 3/2017 |
| WO | WO-2020120542 A2 * | 6/2020 ........... C12Q 1/6869 |

OTHER PUBLICATIONS

Chuang, Cheng-Hsin, et al., "Flexible Piezoelectric Tactile Sensor with Structural Electodes Array for Shape Recognition System," 2008 3rd International Conference on Sensing Techology, Nov. 30-Dec. 3, 2008.

Cockroft, Scott L., et al., "A Single-Molecule Nanopore Device Detects DNA Polymerase Activity with Single-Nucleotide Resolution," J Am Chem Soc. Jan. 23, 2008.

Australian Examination Report No. 2, dated Jun. 30, 2021.

Stranges, P. Benjamin, et al., "Design and characterization of a nanopore-coupled polymerase for single-molecule DNA sequencing by synthesis on an electrode array," PNAS, Oct. 11, 2016, pp. E6749-E6754.

Cockroft, Scott L., et al., "A Single-Molecule Nanopore Device Detects DNA Polymerase Activity with Single-Nucleotide Resolution," NIH Public Access Author Manuscript (Abstract), vol. 130, No. 3, Jan. 1, 2088, pp. 1-9.

* cited by examiner

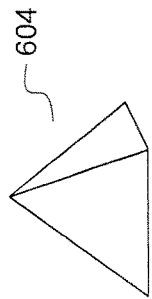
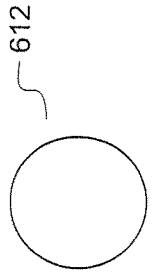
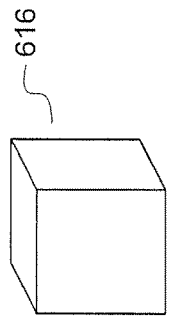
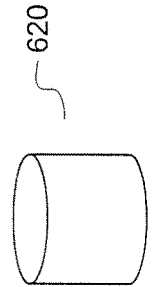
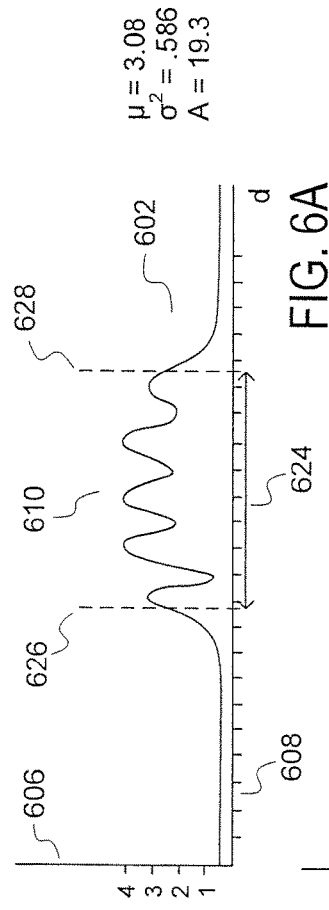
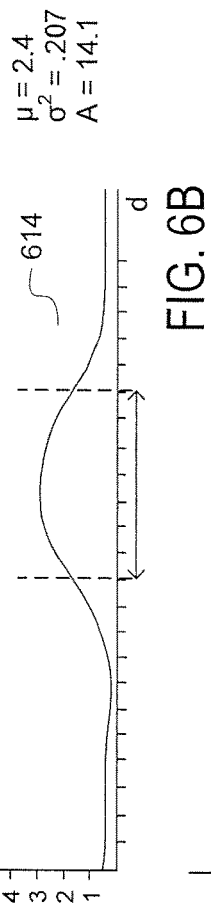
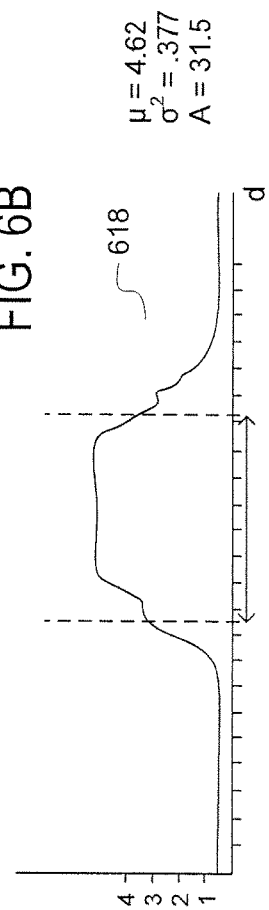
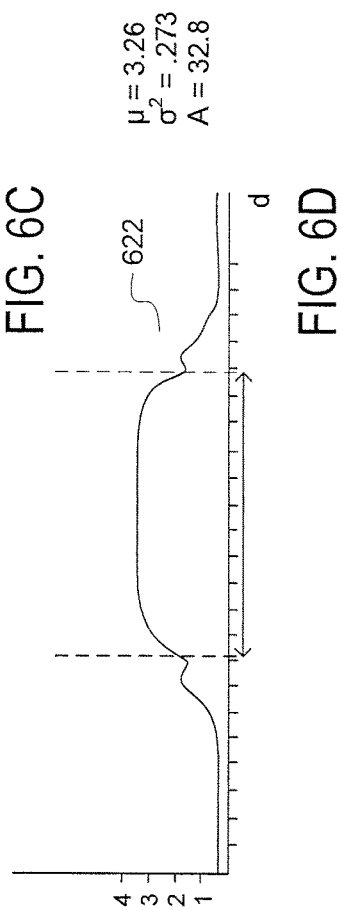
FIG. 6A  FIG. 6B  FIG. 6C  FIG. 6D

| μ | σ² | A |
|---|---|---|
| 3.17 | .261 | 30.9 |
| 3.02 | .262 | 31.7 |
| 3.33 | .281 | 32.8 |
| 3.24 | .275 | 32.9 |
| 3.31 | .280 | 33.2 |
| 3.09 | .276 | 33.6 |
| 3.12 | .271 | 31.1 |
| 3.40 | .273 | 30.2 |
| 3.29 | .265 | 32.9 |
| 3.23 | .269 | 33.8 |
~705
| μ | σ² | A |
|---|---|---|
| 4.77 | .342 | 30.5 |
| 4.51 | .378 | 32.3 |
| 4.32 | .391 | 31.9 |
| 4.65 | .351 | 31.7 |
| 4.17 | .369 | 30.2 |
| 4.31 | .389 | 30.3 |
| 4.40 | .391 | 32.1 |
| 4.67 | .370 | 31.7 |
| 4.71 | .361 | 30.4 |
| 4.49 | .359 | 30.6 |
~704
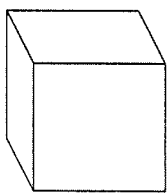
| μ | σ² | A |
|---|---|---|
| 2.61 | .191 | 16.1 |
| 2.52 | .221 | 13.2 |
| 2.58 | .217 | 13.7 |
| 2.32 | .206 | 15.7 |
| 2.41 | .198 | 14.3 |
| 2.45 | .213 | 14.1 |
| 2.37 | .226 | 14.7 |
| 2.55 | .199 | 13.9 |
| 2.52 | .193 | 13.5 |
| 2.64 | .212 | 15.9 |
~703
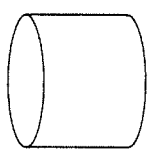
| μ | σ² | A |
|---|---|---|
| 2.85 | .581 | 21.5 |
| 3.10 | .602 | 18.7 |
| 2.91 | .592 | 19.2 |
| 3.32 | .577 | 21.7 |
| 3.21 | .613 | 19.1 |
| 2.97 | .597 | 18.5 |
| 3.06 | .585 | 20.3 |
| 3.17 | .586 | 20.7 |
| 2.92 | .572 | 19.5 |
| 3.27 | .593 | 18.7 |
~702
FIG. 7

| | first implementation (Fig. 5) | second implementation (Fig. 13) |
|---|---|---|
| power source for mechanical translator | battery/line current | dNTP → dNMP monomer + PPi → dNMP monomer + 2Pi 1208 |
| mechanical translator | electric motor/geared drums | Klenow fragment of DNA polymerase I 1210 |
| shape-change component | funnel-shaped set of spring-like bristles | Klenow fragment of DNA polymerase I 1212 |
| coupler | cord/wire | DNA polymer 1214 |
| variable resistor | potentiometer | DNA-polymer subsequence/ MspA-porin constriction 1216 |
| current | electric current | charged-particle current 1218 |
| power source for driving the current | battery/line current | line current 1220 |
| current flow/potential measurement | voltmeter | current-to-voltage converter 1222 |

FIG. 12

| initially fixed parameters | initially fixed but adjustable with lag time | continually tunable parameters |
|---|---|---|
| type of monovalent cation/Cl⁻ salt(s) | T | applied V |
| concentration of monovalent cation/Cl⁻ salt(s) | P | polarity of applied V |
| type of divalent cation /$Cl_2^-$ salt(s) | pH | instrumental parameters |
| concentration of divalent cation/$Cl_2^-$ salt(s) | | |
| type of pH buffer | | |
| concentration of pH buffer | | |
| types and concentration of other buffer constituents (e.g. DTT) | | |
| type of polymerase | | |
| type of porin | | |
| tether | | |
| primer/template type | | |
| primer/template concentration | | |
| bilayer constituents | | |
| types of NTPs | | |
| concentrations of NTPs | | |
| type of electrode | | |
| cell volume | | |
| other cell parameters | | |

2802 — initially fixed parameters
2804 — initially fixed but adjustable with lag time
2806 — continually tunable parameters

FIG. 28

TUNING AND CALIBRATION FEATURES OF SEQUENCE-DETECTION SYSTEM

BACKGROUND

Many different types of sequences of objects or entities are encountered in industrial and research settings. DNA-sequence determination and RNA-sequence determination are employed in many different research, diagnostic, forensic, and pharmaceutical processes and applications. Many sequence-detection systems use multiple types of detectors and multiple types of signals output by the detectors to identify the types of entities and objects within an input target sequence. Often, electromagnetic sensors are used to generate electrical signals that vary with the dimensional and electrical properties of the objects and entities that pass by the electromagnetic sensors. Optical sensors are used, in certain sequence-detection systems, to identify and classify entities and objects within target sequences by the wavelength of light absorbed by the objects or entities or by computational processing of optical images generated from the objects or entities. Additional detectors include weight detectors, volume detectors, and magnetic-susceptibility detectors.

Sequence detectors are often characterized by the reliability and accuracy with which they determine and report the sequences of objects or entities of input targets, by the speed with which input target sequences are identified, and by the cost and complexity of the sequence detectors. Often, increases in reliability and accuracy are accompanied with increases in cost and complexity. In order to optimally employ sequence detectors in real-world applications, systems and process engineers seek to evaluate and compare a variety of different types of sequence detectors for use in particular applications. For this reason, systems and process engineers, researchers, diagnosticians, and other users of sequence detectors continuously seek new and different types of sequence detectors to facilitate identifying and deploying specific sequence-detection processes and systems that best meet sequence-detection parameters and goals for specific applications.

SUMMARY

The current document discusses a detection system comprising a mechanical-change sensor that exhibits one or more mechanical changes when specifically interacting with entities within a target, each entity having a type, a mechanical-change-to-signal transducer that transduces the one or more mechanical changes into a signal, and an analysis subsystem that determines the types of entities within the target using the signal. The current document additionally discusses a sequence-detection system comprising a nucleic-acid-polymerase mechanical-change component that exhibits mechanical changes when specifically associating with nucleotide polyphosphates within an active site; a mechanical-change-to-signal transducer that transduces mechanical changes in the nucleic-acid-polymerase mechanical-change component into an output signal, and an analysis subsystem that determines a sequence of monomer types within a nucleic-acid-polymer target using the output signal. The current document additionally discusses a method for determining a monomer sequence from a signal output by a sequence-detection system, the method comprising identifying portions of the signal that each corresponds to a different monomer in a sequence of monomers, for each signal portion, computing n derived values from the signal portion, wherein n is an integer greater than or equal to 2, mapping the n derived values to an n-dimensional range volume corresponding to a particular type of monomer, and assigning the particular type of monomer to the signal portion, and generating and storing a symbolic representation of a sequence of monomer types complementary to the monomer types assigned to the signal portions. In certain cases, a single derived value may be sufficient to identify the different monomers in a sequence of monomers.

BRIEF DESCRIPTION OF THE DRAWINGS

FIGS. 6A-6D illustrate, in one example, the voltage signals produced by each of the four different types of objects that occur within targets.

FIG. 7 shows hypothetical analytical results produced by the sequence-detection system from a test target that includes 10 objects of each of the four object types a, b, c, and d.

FIG. 12 provides a table that compares an example first sequence-detection system, discussed above with reference to FIGS. 1-11, and an example second sequence-detection system, discussed in the current subsection of the current document.

FIG. 28 lists, in one example, different types of parameters that may be tuned in order to configure, calibrate, and tune operation of the second type of sequence-detection system.

DETAILED DESCRIPTION

Figure 1:
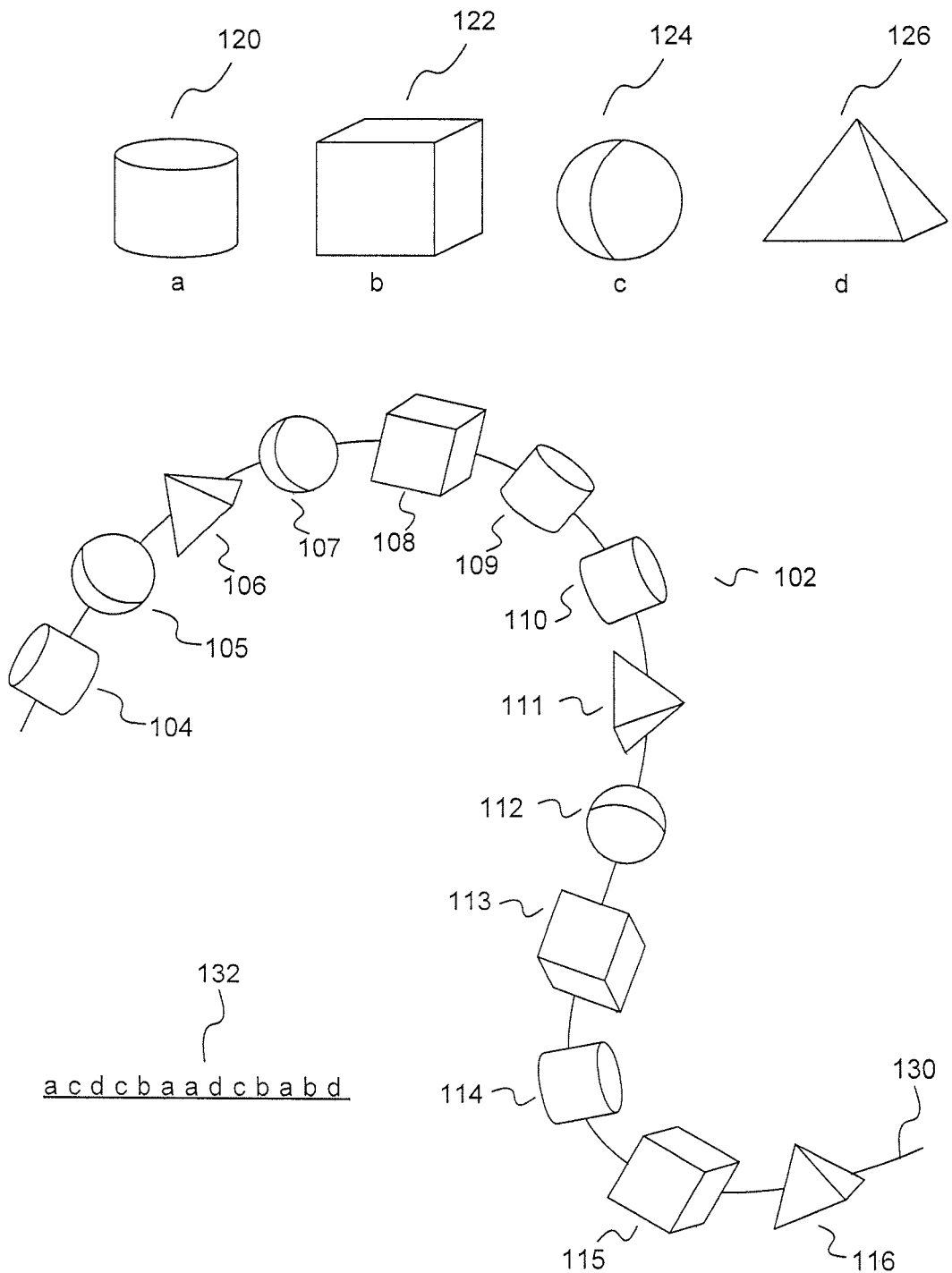
FIG. 1 illustrates, in one example, a target input to, and a determined sequence representation output by, a first type of mechanical-change-based sequence detector.

The current document discusses sequence detectors that generate a signal from which the sequence of types of entities in a target can be determined. A sequence detector described herein may be, for example, an electromechanical device. An electromechanical device is a device that includes both electrical and mechanical components, and that may include additional optical, fluid, and other components. Examples of a sequence detector detect a sequence by generating a signal from which the sequence of entity types in a target can be determined. The sequence detector may include a component, such as a microprocessor-controlled signal-analysis component, that analyzes the signal to determine the sequence of entity types. A target contains a sequence of entities, each entity having a type. A sequence detector physically interacts with a target to generate a signal that varies as a mechanical-change sensor within the sequence detector specifically interacts with different types of entities in the target. A specific interaction is an interaction between the mechanical-change sensor and an entity that deterministically produces a mechanical change in the mechanical-change sensor characteristic of the entity type to which the entity belongs that is then transduced into a corresponding signal by the mechanical-change-to-signal transducer that is also characteristic of the entity type to which the entity belongs. A mechanical change may include a change in shape and/or size of the mechanical-change-to-signal transducer, change in the position of the mechanical-change-to-signal transducer relative to another component, change in the orientation of the mechanical-change-to-signal transducer relative to another component, and other such mechanical changes. In the current document, two different examples of targets and corresponding sequence detectors are discussed in two subsections, below. A first example target is linear sequence of macroscale objects connected together by a string or wire. The objects each have one of four different shapes. The type of an object corresponds to the object's shape. The first corresponding sequence detector produces a time-varying electrical signal as the target passes through a mechanical-change sensor and the mechanical-change sensor specifically interacts with each object, producing a mechanical change in the mechanical-change sensor that is transduced into an electrical signal characteristic of the object's shape by a variable resistor. A second example target is a biopolymer containing a sequence of monomers linked together by covalent bonds. There are four commonly occurring different types of monomers that differ from one another in chemical composition and structure, with additional types of monomers less frequently encountered, in the DNA and RNA polymers used as examples in the following discussion. The second corresponding sequence detector produces a time-varying electrical signal as the target biopolymer passes through a mechanical-change sensor and the mechanical-change sensor specifically associates with monomers to produce a mechanical change in the mechanical-change sensor that is, in turn, communicated to a variable-resistor component by a coupler. These two types of detectors are examples, and other configurations may also exist and be implemented.

A First Type of Mechanical-Change-Based Electromechanical Sequence Detector

FIG. 1 illustrates, in one example, a target input to, and a determined sequence representation output by, a first (type of) mechanical-change-based sequence detector. The target 102 is a linear sequence of objects 104-116. In this example, there are four different types of objects included in the target: (1) a cylindrical-object type 120, referred to as type a; (2) a cubic-object type 122, referred to as type b; (3) a spherical-object type 124, referred to as type c; and (4) a four-sided-pyramid-object type 126, referred to as type d. The target 102 includes a linear spacing member 130, such as a wire or cord, to which the objects 104-116 are securely attached. The target is mechanically input to the first type of sequence detector which outputs a symbolic representation of the sequence of object types 132 within the target.

Figure 2:
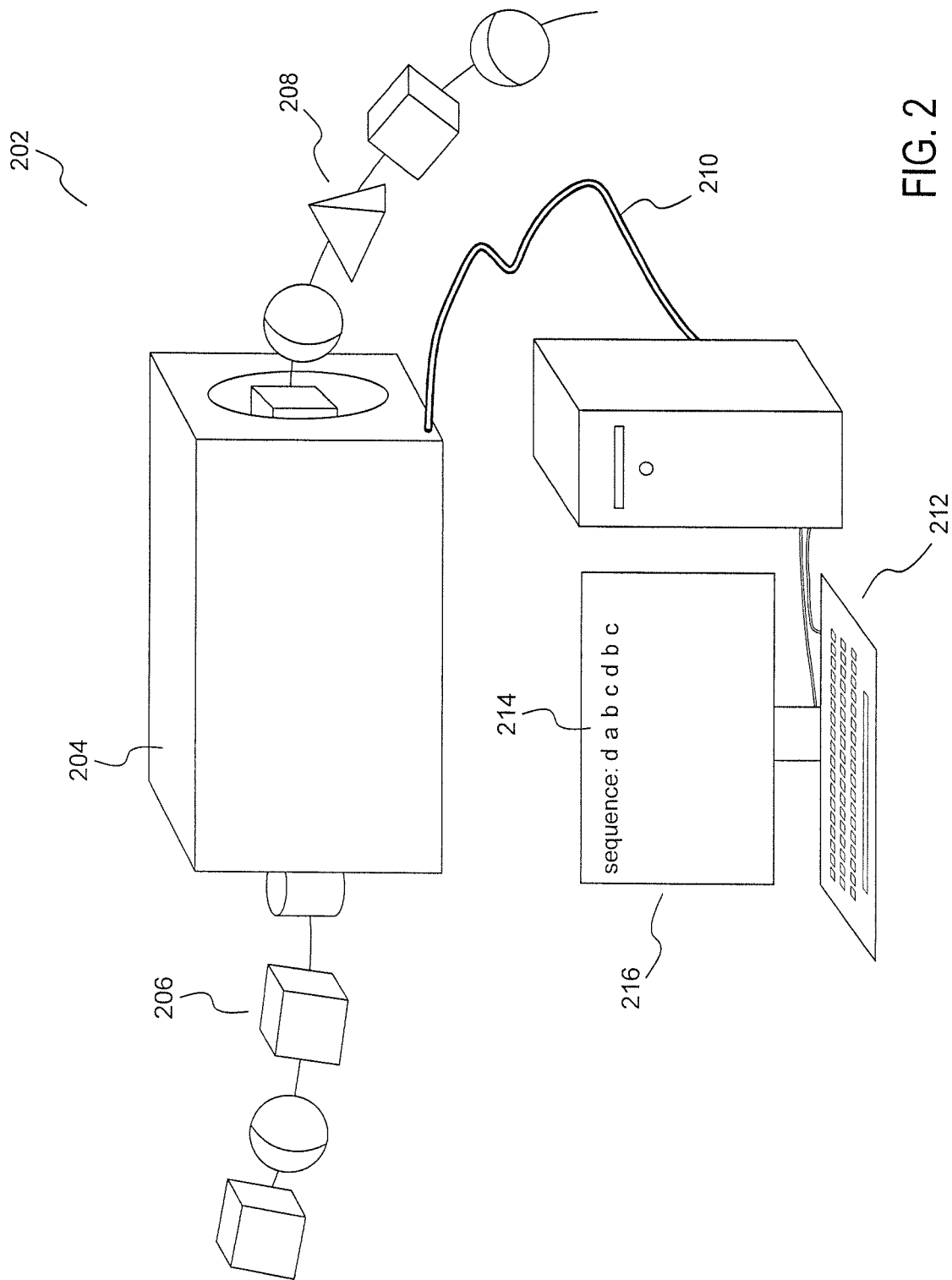
FIG. 2 illustrates one implementation of a sequence-detection system based on the first type of mechanical-change-based sequence detector.

FIG. 2 illustrates one implementation of a sequence-detection system based on the first type of mechanical-change-based sequence detector. The sequence-detection system 202 includes a mechanical-change-based sequence detector 204 into which a target 206 is mechanically input. The mechanical-change-based sequence detector mechanically outputs the target 208 and outputs an electrical signal 210 to an analysis subsystem, implemented as a computer program running on a computer system 212 in certain sequence detectors, which processes the electrical signal to determine the sequence of object types within the target and to output the determined sequence of object types 214 on a computer-display device 216. In alternative implementations, the analysis subsystem is implemented by processor-controlled subsystems other than general-purpose computer systems. The computer system may additionally store an encoded representation of the sequence in one or more memories and/or one or more mass-storage devices. The encoded representation of the sequence may be transmitted to remote computer systems and may be subsequently retrieved for display to a user and for further analysis.

Figure 3C:
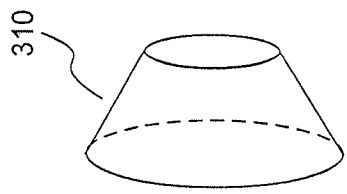
FIGS. 3A-3F illustrates, in one example, the mechanical-change sensor component of the sequence-detection system shown in FIG. 2.
Figure 3B:
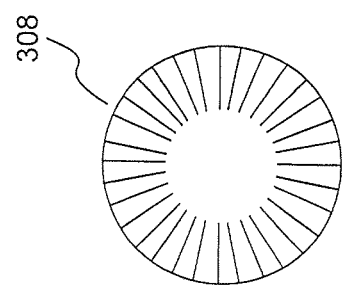
Figure 3A:
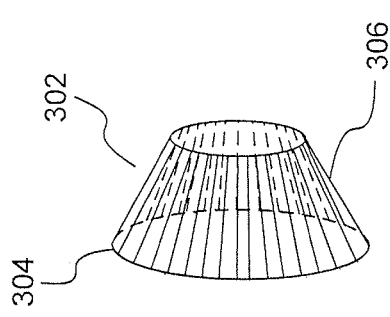
Figure 3F:
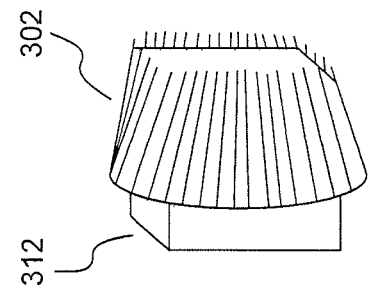
Figure 3E:
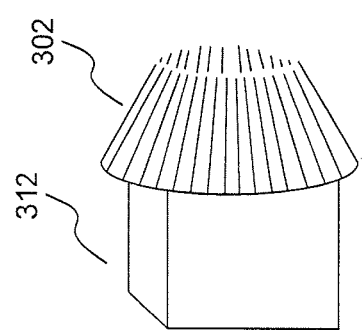
Figure 3D:
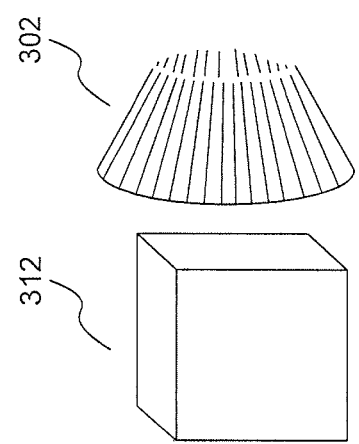

FIGS. 3A-3F illustrates, in one example, the mechanical-change sensor component of the sequence-detection system shown in FIG. 2. As shown in FIG. 3A, the mechanical-change sensor component 302 is a funnel-shaped device comprising a rigid circular ring 304 to which a large number of flexible, spring-like tines, including tine 306, are attached. The tines are arranged as if lying on the surface of a conical section with inward, radial orientations, as shown in a top-down projection view in FIG. 3B. FIG. 3C shows a logical representation of the mechanical-change sensor component 310. In the series of figures comprising FIGS. 3D-3F, operation of the mechanical-change sensor component is illustrated. An object of type b 312 (122 in FIG. 1) is shown positioned behind the mechanical-change sensor component 302 in FIG. 3D. In FIGS. 3E-3F, the object is mechanically translated through the mechanical-change sensor component 302. As it moves through the mechanical-change sensor component, the object pushes the flexible tines outward, as shown in FIG. 3F, distorting of the funnel shape of the mechanical-change component.

Figure 4:
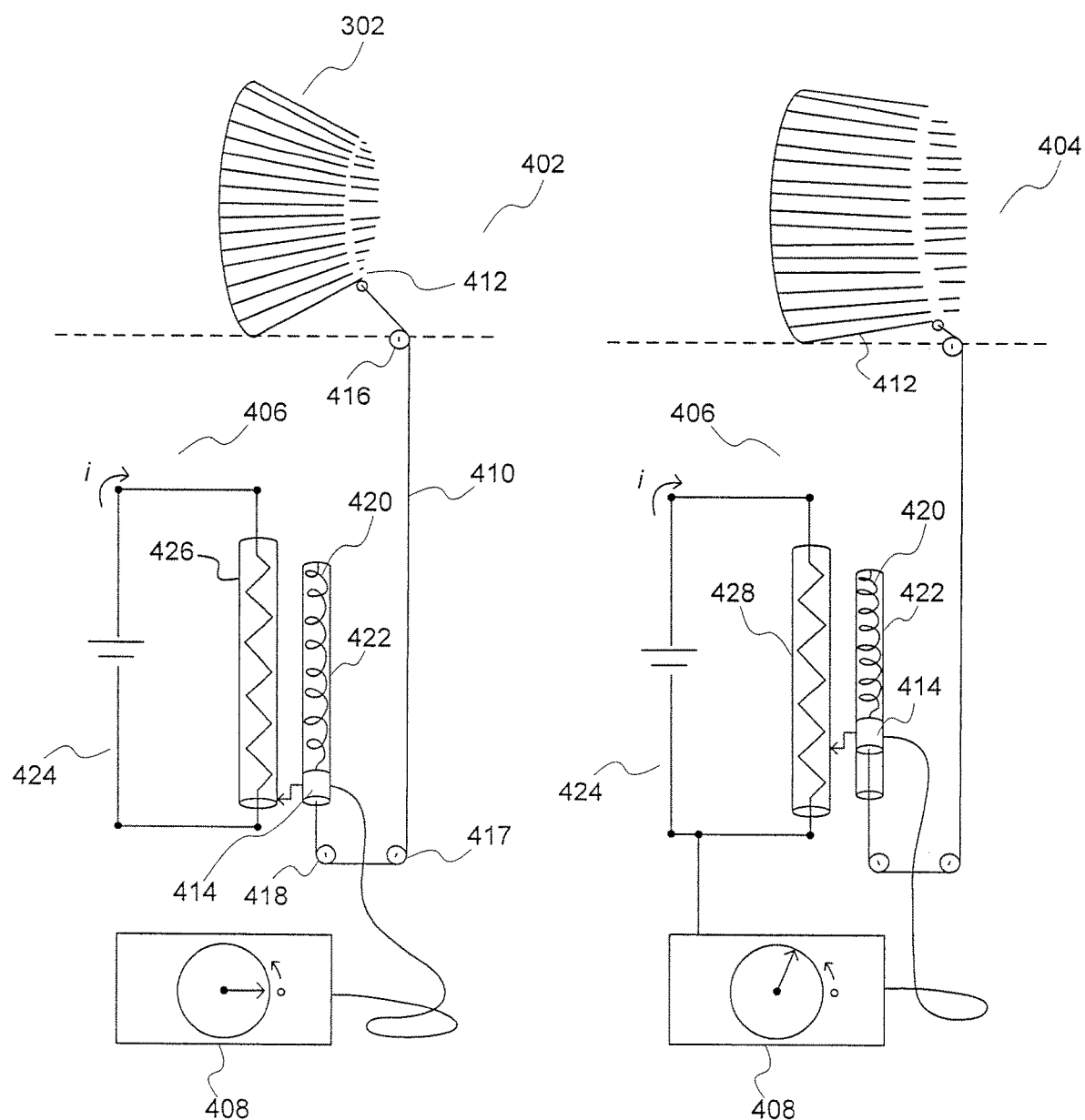
FIG. 4 illustrates, in one example, generation of a voltage signal from changes in the shape of the mechanical-change sensor component by a mechanical-change-detection subsystem within the sequence-detection system shown in FIG. 2.

FIG. 4 illustrates, in one example, generation of a voltage signal from changes in the shape of the mechanical-change sensor component by a mechanical-change-detection subsystem within the sequence-detection system shown in FIG. 2. On the left-hand side of FIG. 4, the mechanical-change-detection subsystem 402 is shown when the funnel-like shape of the mechanical-change sensor component is undistorted. The right-hand side of FIG. 4 shows the mechanical-change-detection subsystem 404 when the funnel-like shape of the mechanical-change sensor component is distorted by the presence of an object within the mechanical-change-sensor component. The mechanical-change-detection subsystem 402 includes the mechanical-change sensor component 302, a potentiometer 406, and a voltmeter 408. The mechanical-change sensor component 302 is mechanically connected to the potentiometer 406 by a cord or wire 410 attached, at one end, to one of the tines 412 of the mechanical-change sensor component and attached to a slidable potentiometer arm 414, at the other end. The cord or wire 410 passes over three freely rotating pulleys 416-418. The slidable potentiometer arm 414 is held in a first position by the tine 412 against the force of a weak spring 420 within a potentiometer-arm cylinder 422. When the mechanical-change sensor component is distorted by the presence of an object, as shown in the right-hand side of FIG. 4, the tine 412 is forced downward, as a result of which the slidable potentiometer arm 414 is pulled upward by spring 420 within the potentiometer-arm cylinder 422. In this example, the potentiometer 406 act as a variable resistor. A variable resistor is a circuit element with a resistance to current flow that can be changed, and a potentiometer is one example of a variable resistor. In the position shown in the left-hand side of FIG. 4, the potentiometer arm is connected to the potentiometer circuit 424 below resistor 426, as a result of which there is little or no voltage drop across the voltmeter 408. However, when the potentiometer arm is in the position shown in the right-hand side of FIG. 4, the potentiometer arm is connected to the potentiometer circuit 424 at a point part way up the resistor 428, as a result of which there is a significant voltage drop across the voltmeter. Thus, the mechanical-change-detection subsystem generates a varying voltage signal in correspondence with a degree of distortion in the shape of the mechanical-change sensor component. The magnitude of the output voltage signal corresponds to the degree of distortion of the mechanical-change sensor component.

Figure 5:
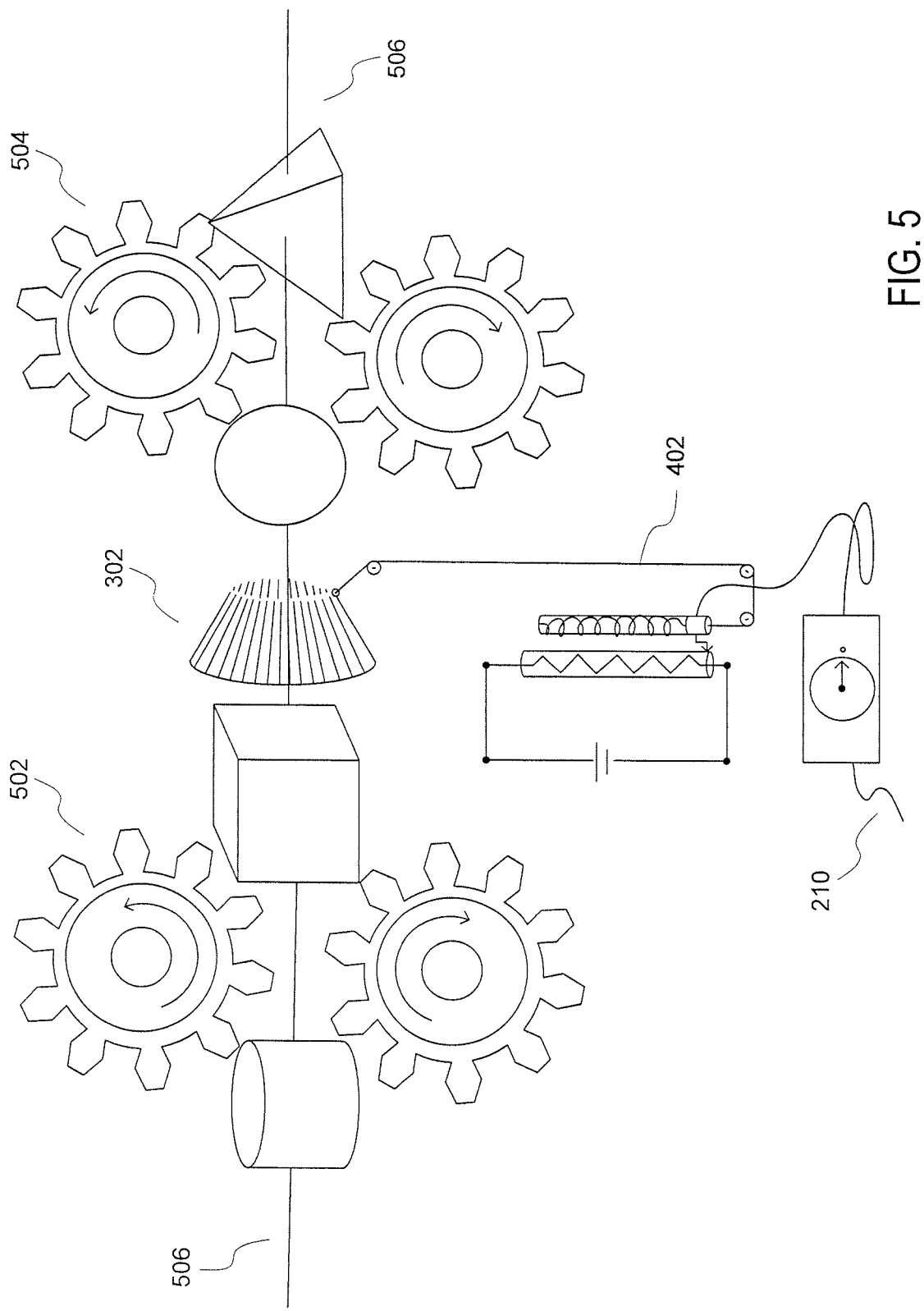
FIG. 5 illustrates, in one example, the internal components of the mechanical-change-based sequence detector 204 shown in FIG. 2.

FIG. 5 illustrates, in one example, the internal components of the mechanical-change-based sequence detector 204 shown in FIG. 2. The mechanical-change-based sequence detector includes the mechanical-change-detection subsystem 402 shown in FIG. 4 and two electric-motor-driven pairs of counter-rotating geared drums 502 and 504 that feed the objects of a target 506 through the mechanical-change sensor component 302. As the target is pulled through the mechanical-change sensor component, the voltmeter outputs a voltage signal 210 that is input to an analysis subsystem (212 in FIG. 2).

FIGS. 6A-6D illustrate, in one example, the voltage signals produced by each of the four different types of objects that occur within targets. FIG. 6A shows a plot 602 of the voltage signal generated when an object of type d 604 passes through the mechanical-change sensor component. The voltage of the output signal is represented by a vertical axis 606 and the position of the object in a horizontal direction is represented by a horizontal axis 608 in the plot. Note that the position may be expressed either in a horizontal displacement or in time, assuming that the target moves through the sensor at a constant velocity. Because objects of type d are rotationally unstable with respect to an internal axis that passes through the top vertex and the center of the base, objects of type d tend to rotate back and forth about this axis as they pass through the mechanical-change sensor component. They also tend to rotate about four internal horizontal axes. As a result, the voltage signal 610 tends to oscillate as the object passes through the mechanical-change sensor. Objects of type c 612 produce a smooth and symmetrical signal 614, as shown in FIG. 6B. Objects of type b 616 show a symmetrical signal 618 with minor oscillations due to slight rotational instability, as shown in FIG. 6C. Objects of type a 620 also produce a symmetrical output signal 622 with slight oscillations, as shown in FIG. 6D. The output voltage signals are analyzed by the computational analysis subsystem (212 in FIG. 2). Data is collected from a region of each voltage-signal curve that begins when the voltage signal rises to half peak height and that ends when the signal falls back to half peak height, shown in each plot of FIGS. 6A-6D by a horizontal double-headed arrow, such as arrow 624, and vertical dashed lines, such as vertical dashed lines 626 and 628. The analysis subsystem computes, from the voltage-signal-magnitude data collected from each object-indicating voltage-signal curve, a mean voltage magnitude $\mu$, such as mean voltage magnitude 630, a variance $\sigma^2$, such as variance 632, and an area A under the voltage-signal curve, such as area 634.

The computed values are obtained by collecting n sample voltage magnitudes $v_i$ from different timepoints or displacements within the central portion of voltage-signal curve. In various different implementations, current magnitudes or other values may be instead sampled. A sampling rate of 1 KHz, for example, would provide 1000 sample voltage magnitudes. The area A is computed by discrete integration:

$$A = \sum_{i=1}^{n} v_i.$$

The mean voltage magnitude is computed as:

$$\mu = \frac{\sum_{i=1}^{n} v_i}{n}.$$

The standard deviation is computed as:

$$\sigma^2 = \frac{\sum_{i=1}^{n} (v_i - \mu)^2}{n}.$$

Finally, the standard deviation is computed as:

$$\sigma = \sqrt{\sigma^2}.$$

FIG. 7 shows hypothetical analytical results produced by the sequence-detection system from a test target that includes 10 objects of each of the four object types a, b, c, and d. The analytical results for each of the four types of objects are shown in tables 702-705. Each table includes three columns corresponding to the computed voltage-magnitude mean, variance, and area for each voltage-signal curve output by the mechanical-change-based sequence detector. As commonly occurs in experimental data, the three computed values vary across the 10 instances of the four different types of objects. The analysis subsystem attempts to use the output voltage-signal curves to uniquely identify the type of each object passing through the mechanical-change sensor component.

Figure 8:
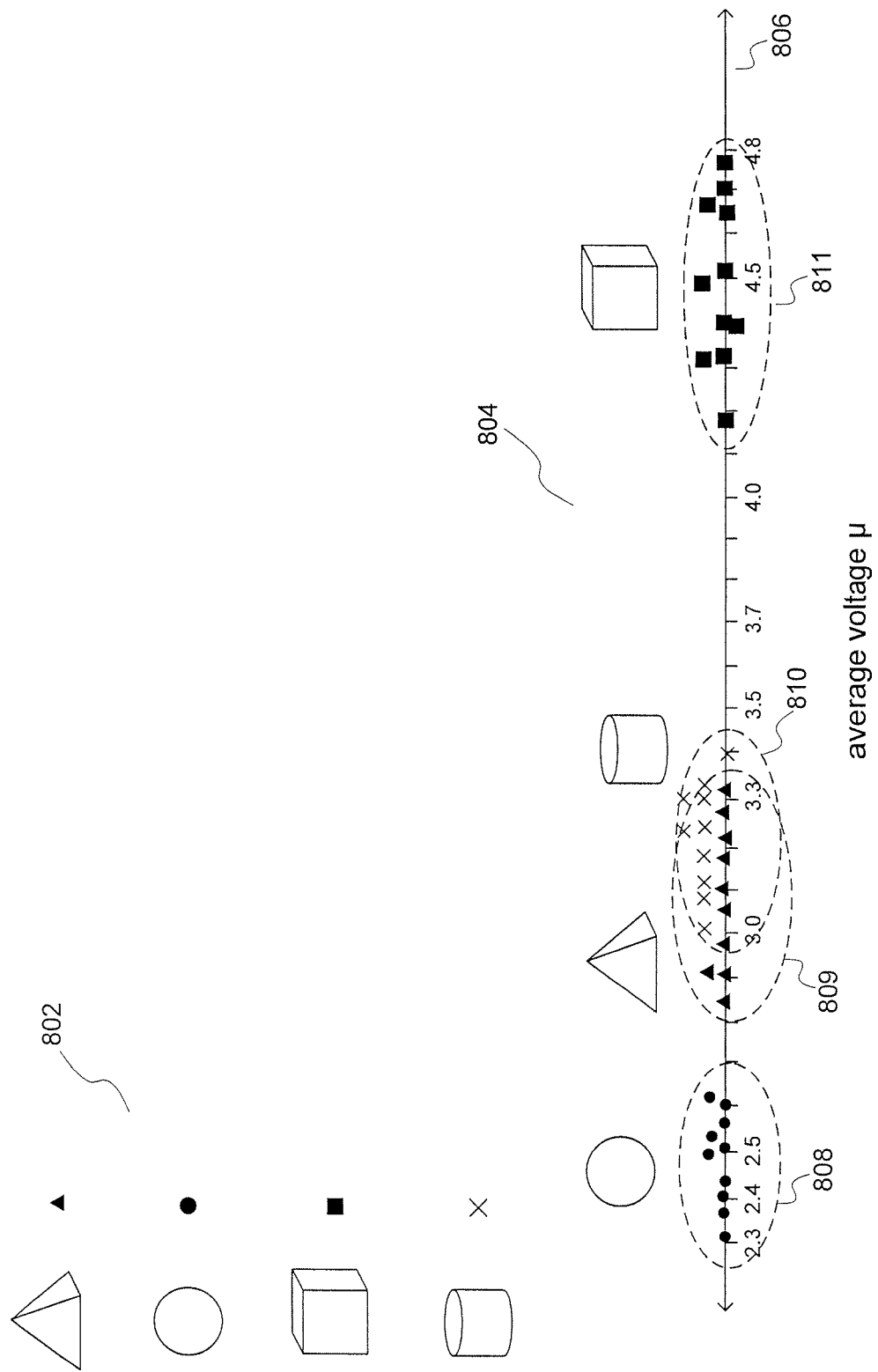
FIG. 8 shows a plot of the mean-voltage-magnitude data contained in the data tables shown in FIG. 7.

A common approach for using output voltage signals is to choose a single computed value, such as the mean voltage magnitude, to differentiate each type of object from the remaining types of objects. FIG. 8 shows a plot of the mean-voltage-magnitude data contained in the data tables shown in FIG. 7. A key 802 is shown in the upper left-hand portion of FIG. 8. The key describes the different symbols used for plotting mean-voltage-magnitude values for each of the different types of objects. The lower portion of FIG. 8 shows a plot 804 of the mean-voltage-magnitude data with respect to a horizontal axis 806 representing voltage magnitude. The mean-voltage-magnitude values for each different type of object cluster within subregions of the horizontal axis, as indicated in FIG. 8 by the dashed ellipses 808-811. The mean voltage magnitudes for objects of type c fall within the voltage-magnitude range indicated by ellipse 808, for example. From the data plot shown in FIG. 8, objects of type c are uniquely distinguishable from the remaining object types based on mean voltage magnitude, alone, since in this example there is no overlap between the range of mean voltage magnitudes for objects of type c and the ranges of mean voltage magnitude for objects of type a, b, and d. Similarly, objects of type b, the mean-voltage-magnitude values of which fall within the range represented by ellipse 811, are uniquely distinguishable from the remaining types of objects based on mean voltage magnitude, alone. However, the mean-voltage-magnitude ranges for objects of type d and a, represented by ellipses 809-810, almost completely overlap with one another, as a result of which it is not possible to distinguish between objects of type d and a using mean-voltage-magnitude values, alone.

Figure 9:
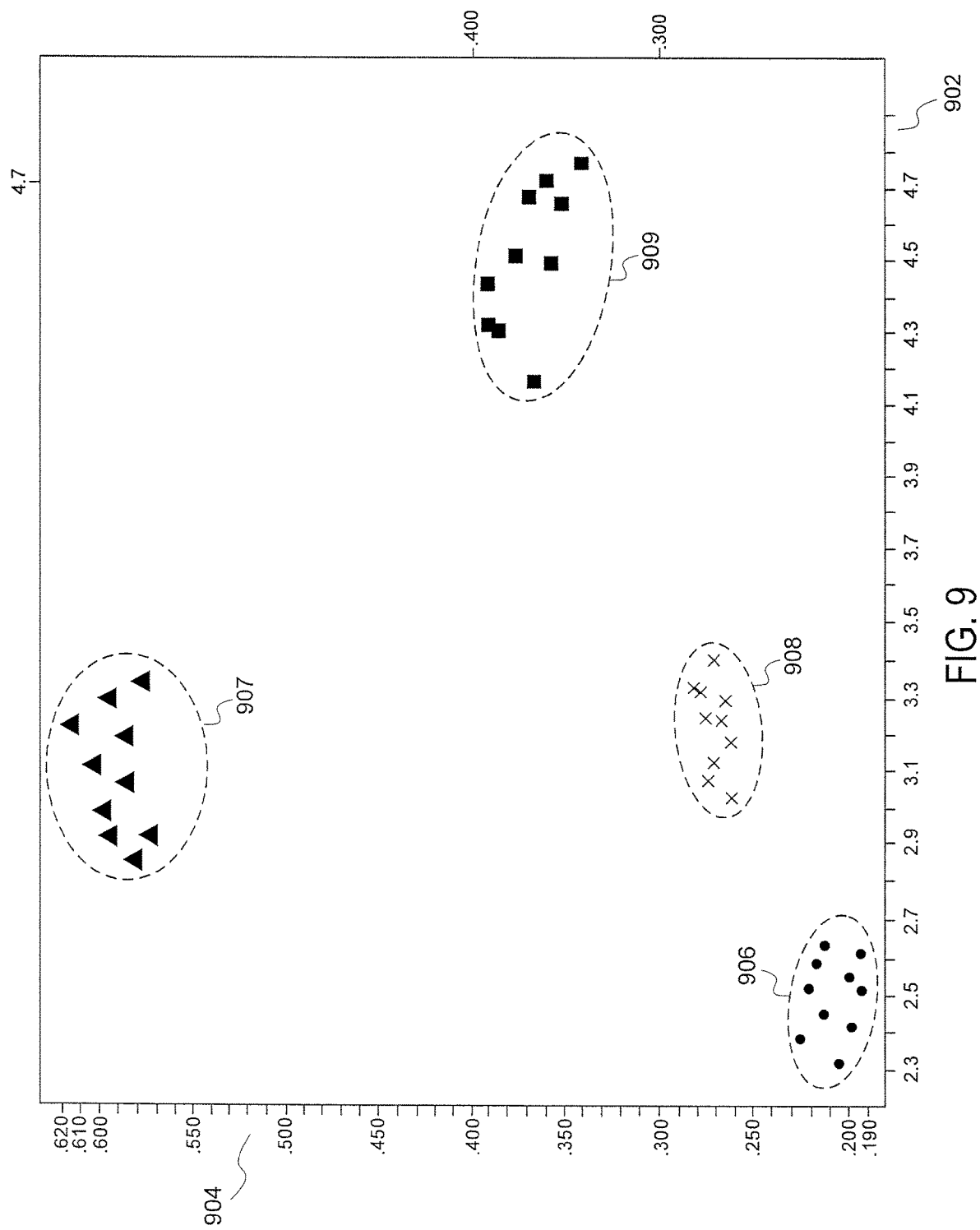
FIG. 9 shows a two-dimensional plot of the data contained in the tables shown in FIG. 7.

In some examples, when a particular output signal is insufficient for distinguishing the different types of objects in a sequence, a sequence-detector designer would seek to incorporate an additional type of sensor into the sequence detector to produce an additional output signal, so that the combination of multiple output signals provides sufficient information for distinguishing the objects from one another. For example, change counters use separate size-detection sensors, weight detectors, and magnetic-susceptibility detectors to produce separate output signals that together provide an unambiguous output-signal-derived fingerprint for each type of coin. By contrast the currently described example sequence-detection systems compute multiple derived values from a single output voltage signal in order to differentiate each type of object in a target. As discussed above with reference to FIGS. 6A-6D and FIG. 7, the analysis subsystem computes not only the mean voltage magnitude from the voltage-signal curve corresponding to an object, but also the variance. FIG. 9 shows a two-dimensional plot of the data contained in the tables shown in FIG. 7. The horizontal axis 902 represents the mean voltage magnitude obtained from voltage-signal curve, as in FIG. 8, and the vertical axis 904 represents the variance obtained from the voltage-signal curve. As in FIG. 8, dashed ellipses 906-909 surround clusters of data points plotted for each of the different object types. As can be easily seen in FIG. 9, the two-dimensional areas contained within these ellipses do not overlap. Thus, a pair of mean-voltage-magnitude and variance values computed from the single output voltage signal for a particular object contains sufficient information to unambiguously assign a type to the object. In other words, in this example the single output voltage signal produced by the mechanical-change-detection subsystem contains sufficient information for assigning a type to each object, but the information within each voltage-signal curve is, in a sense, two-dimensional.

Figure 10:
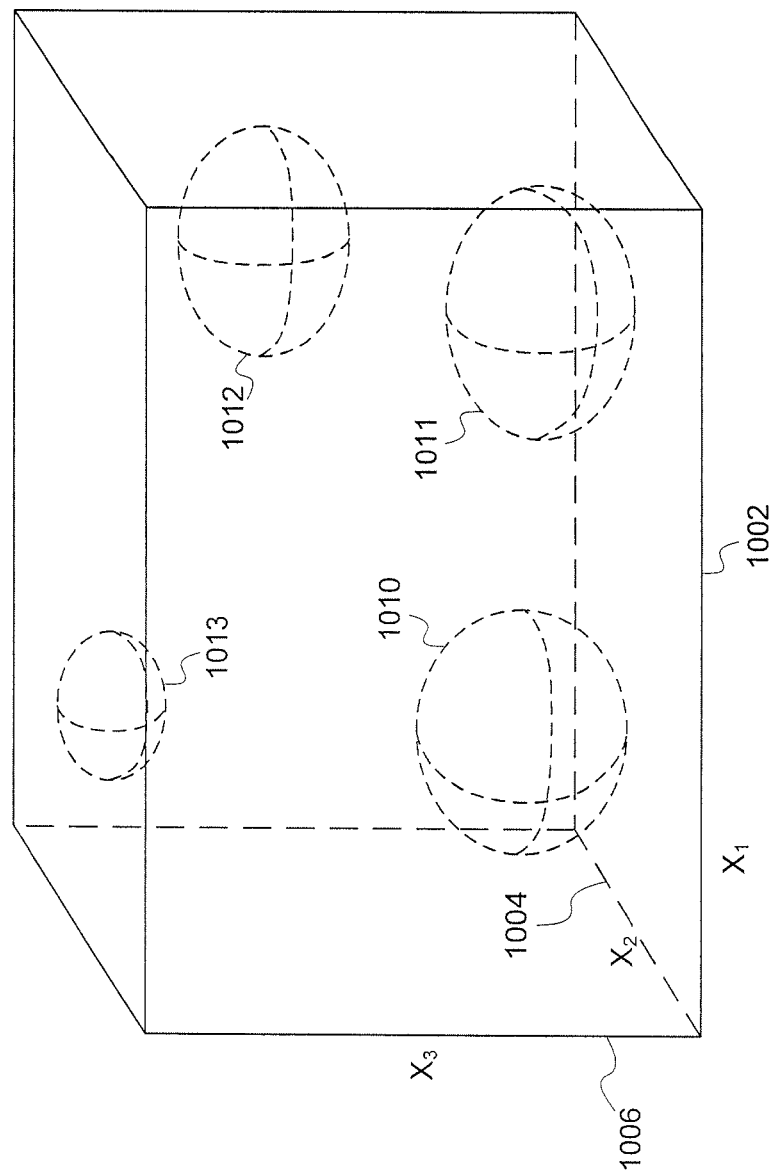
FIG. 10 illustrates, in one example, use of three derived values for determination of object types.

As discussed above with reference to FIG. 9, use of the two derived values, including mean voltage magnitude and variance, by the analysis subsystem of the sequence-detection system is sufficient, for the target described with reference to FIG. 1, to identify each object or entity within the target. The analysis system uses the two derived values as coordinates to map the two derived values to a range area corresponding to a particular object or entity type. Were the range areas overlapping, then an additional derived value, such as the computed area below the voltage-signal curve, might be used to uniquely differentiate object types within targets. FIG. 10 illustrates, in one example, use of three derived values for determination of object types. In FIG. 10, each of three different derived values are represented by the three axes 1002, 1004, and 1006. Plotted data points for the four different object types fall into the four discrete and nonoverlapping elliptical range volumes 1010-1013. Generally, as the number of derived values is increased, the probability of overlap in the ranges of the derived values for the different object types decreases when the derived signals are reasonably orthogonal and sensitive to differences in object type.

Figure 11:
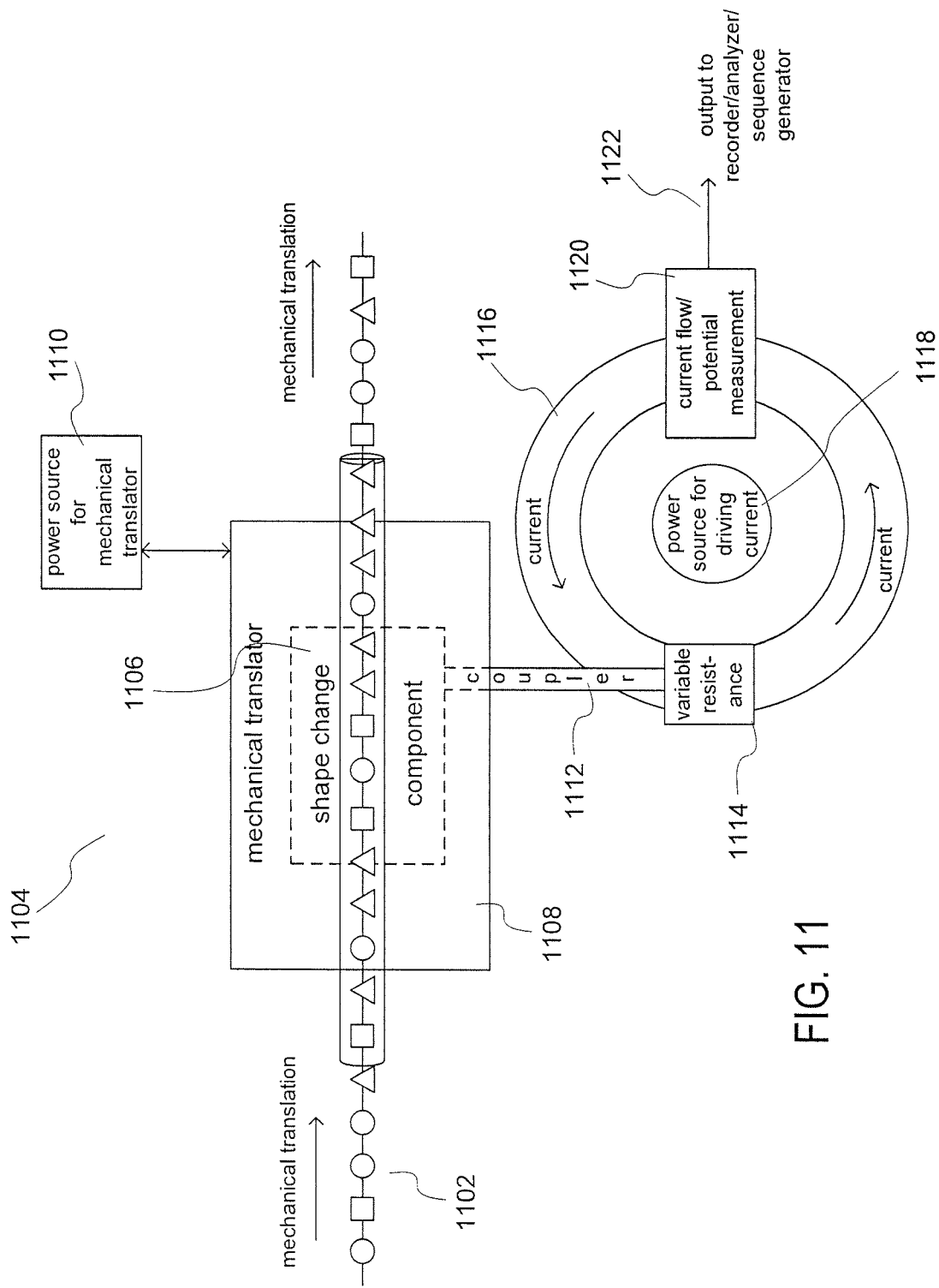
FIG. 11 summarizes the sequence detection system discussed above with reference to FIGS. 1-10.

FIG. 11 summarizes the sequence detection system discussed above with reference to FIGS. 1-10. A target comprising a sequence of objects or entities 1102 is input to the sequence-detection system 1104 and is mechanically translated through a mechanical-change component 1106 by a mechanical-translator component 1108. A power source 1110 provides power for the mechanical translation. The mechanical-change component 1106 is mechanically coupled, by a coupler 1112, to a variable-resistance component 1114. A mechanical coupler joins two or more entities by a physical coupler, such as a string or cord, in a macroscale device, or a linear molecule, such as a DNA polymer, in nanoscale and microscale devices. The variable-resistance component 1114 provides a variable resistance to a current flow 1116 in response to motion of the coupler 1112, in turn induced by changes in the shape of the mechanical-change component 1106. A power source 1118 drives the current flow 1116. The measurement component 1120 measures the potential in the current-flow channel or the current flow, itself, to produce an output electrical signal 1122 that varies with variation of the shape of the mechanical-change component 1106. The output signal is computationally processed by an analysis subsystem, not shown in FIG. 11, to generate a representation of the sequence of object types in the target 1102. The sequence-detection system, discussed above with reference to FIGS. 1-11, is a macroscale device that determines the sequence of macroscale-object types within a target.

A Second Type of Mechanical-Change-Based Electromechanical Sequence Detector

The second (type of) sequence-detection system discussed in the current document is a mixed-scale device that includes macroscale, microscale, and nanoscale components. The second sequence-detection system determines the sequence of deoxynucleotide monomers within nucleic-acid polymers.

FIG. 12 provides a table that compares the first sequence-detection system, discussed above with reference to FIGS. 1-11, and the second sequence-detection system, discussed in the current subsection of the current document. A first column 1202 in the table lists sequence-detection-system components, discussed above with reference to FIG. 11. A second column 1204 of the table further describes each of the components listed in the first column with respect to the first sequence-detection system. A third column 1206 further describes each of the components listed in the first column with respect to the second sequence-detection system, further described below. In the first sequence-detection system, the power source for mechanical translation of the target is an electrical current obtained from a battery or from line current while, in the second sequence-detection system, the power source for mechanical translation of the target is chemical energy produced by hydrolysis of a phosphoanhydride bond and hydrolysis of inorganic pyrophosphate, as indicated in the first row 1208 of the table. In the first sequence-detection system, the mechanical translator that translates the target is two pairs of counterrotating electric-motor-driven geared drums while, in the second sequence-detection system, the mechanical translator is a Klenow fragment of *E. coli* DNA polymerase I, as indicated in the second row 1210 of the table. In the first sequence-detection system, the mechanical-change component is a funnel-shaped set of spring-like bristles, or tines, while, in the second sequence-detection system, the mechanical-change component is a Klenow fragment of DNA polymerase I, as indicated in the third row 1212 of the table. In the first sequence-detection system, the coupler is a cord or wire while, in the second sequence-detection system, the coupler is a DNA polymer, as indicated in the fourth row 1214 of the table. In the first sequence-detection system, the variable resistor is a potentiometer while, in the second sequence-detection system, the variable resistor is a portion of the DNA-polymer coupler lying within an MspA-porin channel, as indicated in the fifth row 1216 of the table. In both sequence-detection systems, the current is an electrical current. In the first sequence-detection system, the charge carriers are conduction-band electron flowing through a metal wire while, in the second sequence-detection system, the charge carriers are positively and negatively charged ions, as indicated in the sixth row 1218 of the table, although, of course the electrodes are connected by current-carrying wires. In the first sequence-detection system, the power source for driving the current is obtained from a battery or from line current while, in the second sequence-detection system, the power source for driving the current is obtained from line current, as indicated in the seventh row 1220 of the table. In the first sequence-detection system, the current-flow or potential measurement device is a voltmeter while, in the second sequence-detection system, the current-flow or potential measurement device is a current-to-voltage converter, as indicated in the eighth row 1222 of the table. The first and second sequence-detection systems are thus similar to one another in configuration and operation, but include different specific types of components.

Figure 13:
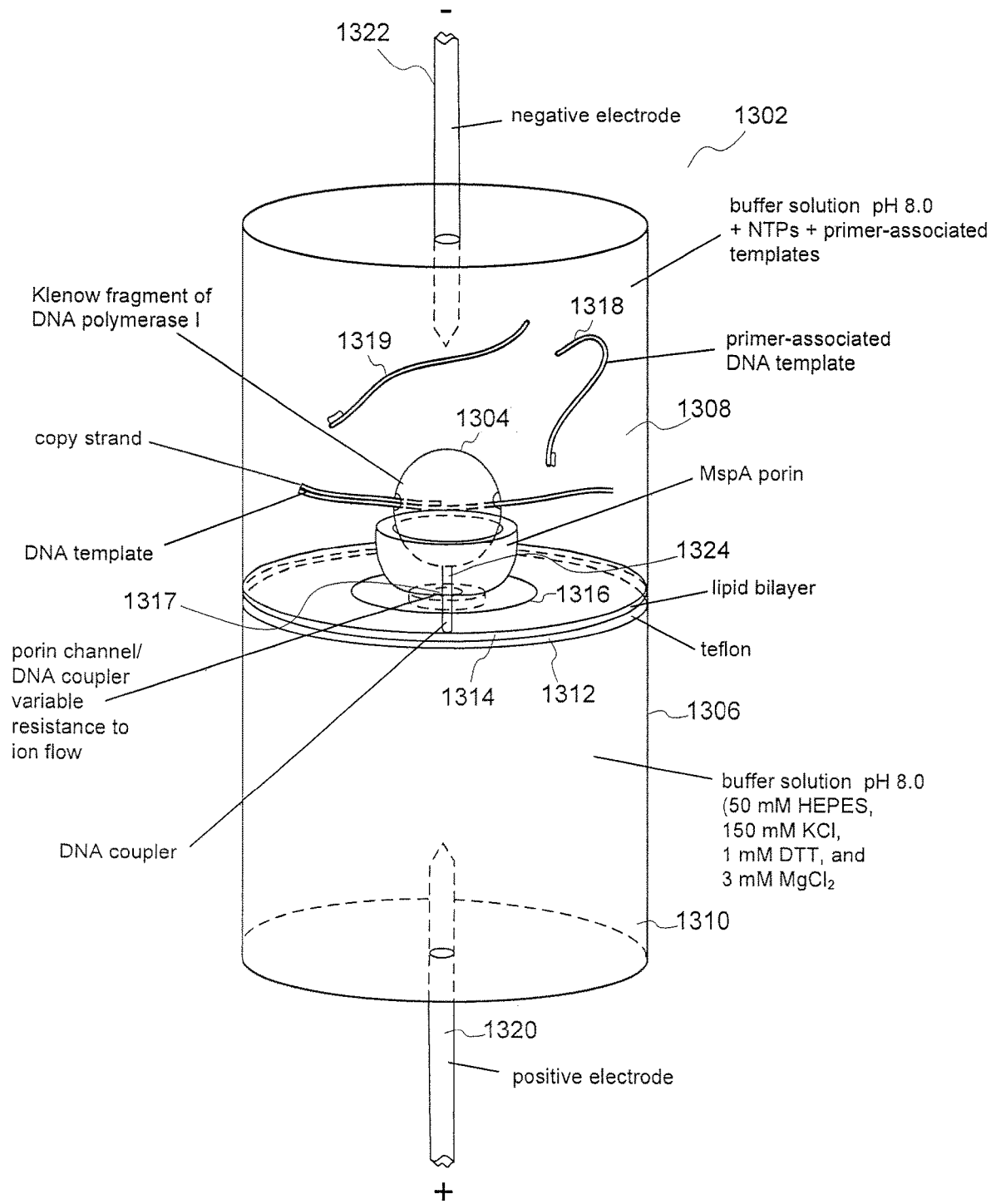
FIG. 13 illustrates, in one example, a mechanical-change-based sequence detector that is included in the second sequence-detection system.

FIG. 13 illustrates, in one example, a mechanical-change-based sequence detector that is included in the second sequence-detection system. In the following discussion, the mechanical-change-based sequence detector 1302 is referred to as a "cell." The illustration in FIG. 13 does not reflect the relative sizes and volumes of the various components. In many implementations, the cell 1302 is a macroscale or microscale device while the mechanical-change sensor component 1304 is a nanoscale component. FIG. 13 is intended to illustrate the overall configuration and relative positions and orientations of the various components of the mechanical-change-based sequence detector, rather than to accurately portray the relative scales of the components.

The cell 1302 includes a two-part vessel 1306, with a first solution-containing chamber 1308 separated from a second solution-containing chamber 1310 by a Teflon barrier 1312 and a lipid bilayer 1314. In one implementation, the lipid bilayer comprises 1,2-diphytanoyl-sn-glycerol-3-phosphocholine. The Teflon barrier includes an aperture 1316 that is covered by the lipid bilayer, so that the first solution-containing chamber 1308 and the second solution-containing chamber 1310 are separated only by the lipid bilayer within the aperture 1316. A narrow channel 1316 through the lipid bilayer is provided by a Mycobacterial porin ("MspA porin"), an octameric protein aggregate with eightfold rotational symmetry. The narrow channel is sufficiently wide to allow for passive diffusion of ions between the two solution-containing chambers. The first and second solution-containing chambers 1308 and 1310 contain a buffer solution at pH 8.0. In one implementation, the buffer solution includes 50 mM 4-(2-hydroxyethyl)-1-piperazineethanesulfonic acid ("HEPES"), 150 mM KCl, 1 mM dithiothreitol ("DDT"), and 3 mM $MgCl_2$. HEPES is a zwitterionic buffering compound. KCl provides ions that carry ionic current. Dithiothreitol is a reducing agent that promotes free sulfhydryl groups in proteins. $MgCl_2$ contributes $Mg^{2+}$ ions that aids the catalytic activity of the mechanical-change sensor component 1304, discussed below. The first solution-containing chamber 1308 additionally contains deoxynucleotide triphosphates and primer-associated deoxyribonucleic-acid templates. The primer-associated deoxyribonucleic-acid templates 1318-1319 are the targets for which sequences of deoxynucleotide monomers are determined by the second sequence-detection system. In certain implementations, the second solution-containing chamber 1310 additionally contains locking components, discussed below. The solution within the second solution-containing chamber 1310 is in fluid contact with a positive electrode, or reference electrode 1320, and the solution within the first solution-containing chamber 1308 is in fluid contact with a negative electrode 1322. In one implementation, silver/silver-chloride electrodes are used. When a voltage is applied across the cell through the electrodes, negative ions flow through the porin channel towards the positive anode and positive ions flow through the porin channel towards the negative electrode. In one example, the downward flow of negative ions may be inhibited when a DNA or RNA polymer is resident within the pore. In other words, an electrical current is established within the porin channel by application of a voltage across the two electrodes 1320 and 1322. As further discussed below, the polarity of the applied voltage may be temporarily reversed, at various times during operation of the cell, by reversing the polarities of the electrodes.

In alternative implementations, rather than using a Teflon barrier and lipid bilayer, the aperture is produced in a silicon substrate or other type of substrate using a photolithographic process and a synthetic-polymer membrane is employed to prevent fluid communication between the two chambers except through the porin channel. As one example, a triblock copolymer may be used for the membrane. In alternative implementations, MspA-porin variants may be employed, including a single-chain version or a version with fewer or greater than 8 subunits. Certain variants may comprise multiple subunits that differ in sequence. Other types of pore-containing biopolymers and synthetic polymers may alternatively be used in alternative implementations. Additional types of divalent metal ions may also be used, in alternative implementations, including $Mn^{2+}$. Non-catalytic metal ions, including $Ca^{2+}$ and $Sr^{2+}$ may also be used, in certain circumstances.

The mechanical-change sensor component 1304 is, in one implementation, a Klenow fragment of *E. coli* DNA polymerase I. The Klenow fragment may be obtained by removing the 5'→3' exonuclease structural domain from *E. coli* DNA polymerase I by treatment with a protease or by expressing the desired fragment from a genetically modified bacterial strain. The Klenow fragment retains the 5'→3' polymerization functionality. As discussed further, below, when supplied with a primer-associated DNA template and deoxynucleotide triphosphates, the Klenow fragment of *E. coli* DNA polymerase I catalyzes sequential polymerization of the deoxynucleotide triphosphates to form a copy DNA strand complementary in sequence to the template DNA strand. The coupling component 1324 is a DNA-polymer tether. It is attached to the mechanical-change sensor component 1304 and pulled into the porin channel by the voltage applied to the electrodes, since DNA polymers are negatively charged and migrate towards the positive electrode under an applied voltage. A small region of the DNA-polymer tether spanning a narrow constriction within the porin channel, along with the narrow constriction, act together as a variable resistor that regulates the flow of ions between the two solution-containing chambers to different extents depending on the position of the small region of the DNA-polymer tether relative to the narrow constriction, as further discussed below. Because the system comprising the Klenow fragment of *E. coli* DNA polymerase I and the porin exhibits differences for each different type of deoxynucleotide triphosphate that occupies the active site within the Klenow fragment of *E. coli* DNA polymerase I, the DNA-polymer tether has a different dynamic position relative to the narrow constriction within the porin channel when different deoxynucleotide triphosphates are specifically associated with the active site, which is reflected in a different dynamic current flow through the porin channel for each different type of deoxynucleotide triphosphate sequentially incorporated within the growing DNA copy strand.

Specific association between a molecule and an active site involves a key-in-lock or induced-fit type of association in which particular electrostatic and chemical features of the molecule associate with complementary electrostatic and chemical features of the active site, leading to larger binding affinities for the molecule or a class of molecules than for molecules that do not specifically associate with the active site. The differences may result from one or more of conformational changes, movement of the Klenow fragment relative to the porin channel, and other changes. Current-detection circuitry, discussed below, produces a voltage signal that varies in correspondence with variation in the current flow through the porin channel. In alternative implementations, many different polymerases, polymerase fragments, and other types of biomolecules that interact with the biopolymer target for sequencing may be used in place of the above-discussed Klenow fragment. Different types of natural and synthetic nucleotides may be used, including nucleotides with larger phosphate esters, such as deoxynucleotide hexaphosphates, with different carbohydrate components, with different bases, and different functional groups. Many additional types of mechanical-change components may be used for sequencing a variety of different types of target biopolymers and synthetic polymers, including enzymes and other proteins and protein/nucleic-acid complexes that interact with target proteins in sequence-specific fashions. In addition, it is important to note that the phrase "mechanical-change sensor component," when applied to the second sequence-detection system, indicates signal generation is a product of one or more of changes in the shape of the polymerase fragment, changes in the relative positions the polymerase fragment with respect to the porin, and/or changes in the orientations of the polymerase fragment with respect to the porin, as one example. In certain implementations, changes in the shape of the polymerase fragment provide the mechanical changes that lead to movement of the variable resistor. Ultimately, the mechanical-change sensor component, and interactions of the mechanical-change sensor component with the target and with the pore-containing component, produce a mechanical change in the position of the variable resistor. Coupling connectors and variable resistors other than DNA polymers may be used in alternative implementations.

Although the first sequence-detection system is a macroscale system and the second sequence-detection system is a mixed-scale system that includes macroscale and nanoscale components, the second sequence-detection system is analogous to the first sequence-detection system. Both sequence-detection systems employ a mechanical-change sensor component to generate a mechanical signal that varies with the type of object or entity currently being processed by, or associated with, the mechanical-change sensor component. Both sequence-detection systems employ mechanical coupling to couple the mechanical-change sensor component to variable-resistance component. Both sequence-detection systems generate an output voltage signal by transduction of the mechanical signal produced by the mechanical-change sensor component into an electrical signal. Both sequence-detection systems employ computational analysis of the output signal to generate multiple derived values that are used together to identify the sequence of types of objects or entities in a target sequence. In the second sequence-detection system, the sequence of deoxynucleotide-monomer types detected is complementary to, and has reverse polarity with respect to, the sequence of deoxynucleotide-monomer types within the template-strand target.

Figure 14A:
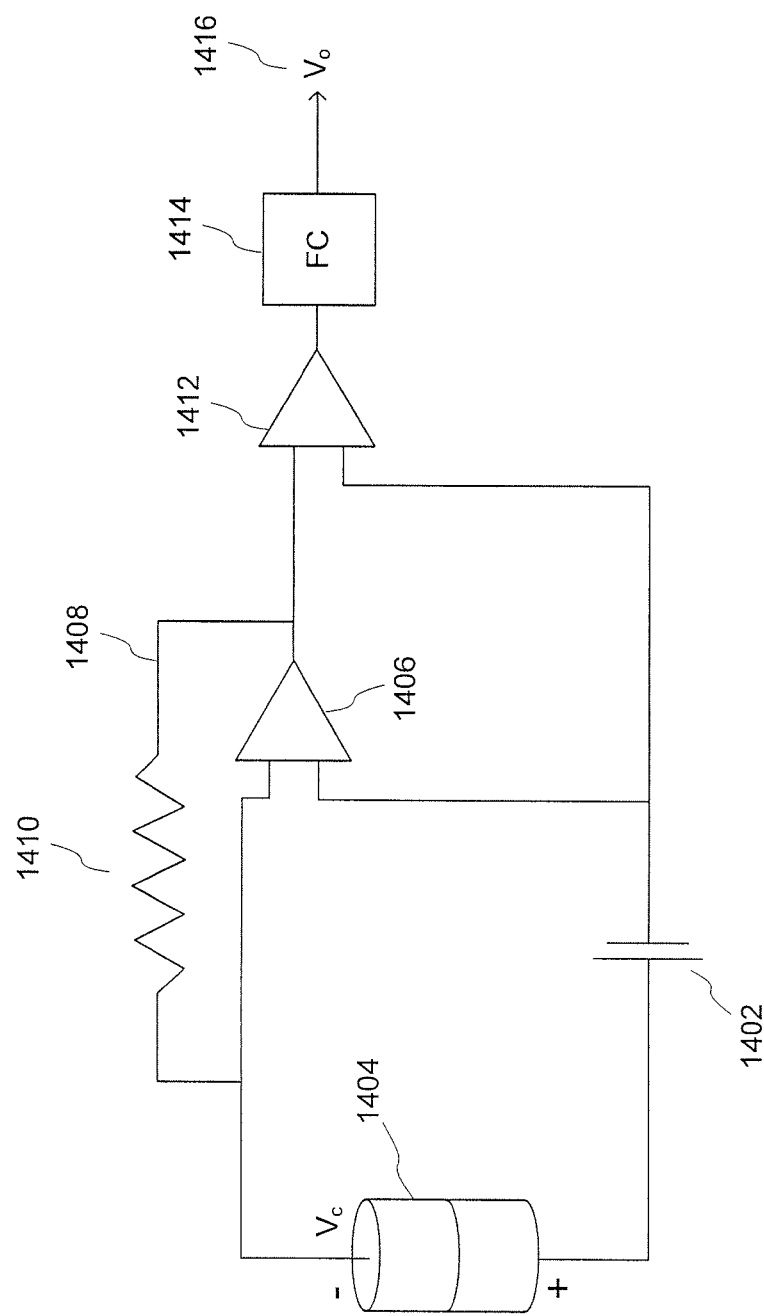
FIGS. 14A-14B illustrate two different current-to-voltage converter circuits that are used separately or together in various implementations of the second sequence-detection system.
Figure 14B:
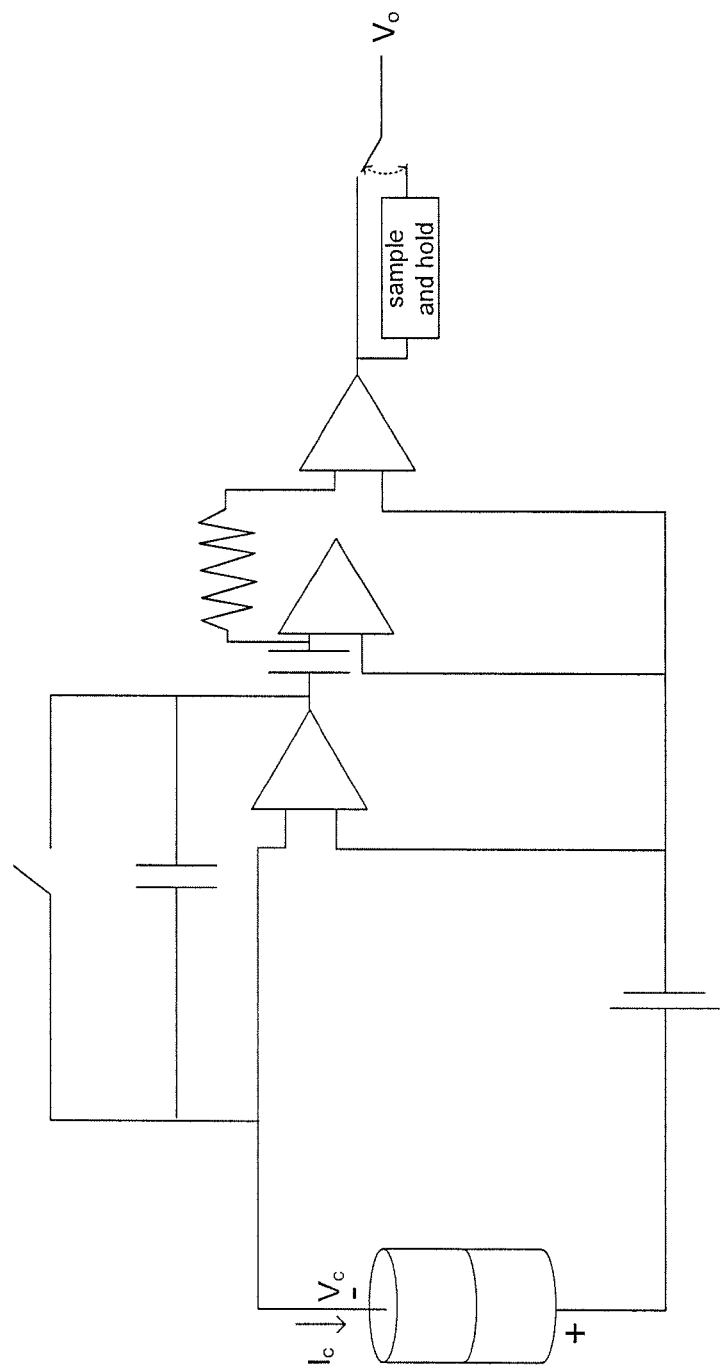

FIGS. 14A-14B illustrate two different current-to-voltage converter circuits that are used separately or together in various implementations of the second sequence-detection system. In FIG. 14A, a voltage source 1402 applies a voltage across the cell 1404. An inverting amplifier, or op amp, 1406 with a feedback loop 1408 containing a feedback resistor 1410 outputs a voltage signal proportional to the current flowing through the cell. A second op amp 1412 amplifies the voltage differential of its inputs to generate an amplified voltage signal that is passed through a frequency-correction circuit 1414 to produce a final output voltage signal 1416 proportional to current flow through the cell 1404. FIG. 14B shows a current-to-voltage converter that uses a feedback capacitor rather than a feedback resistor.

Figure 15:
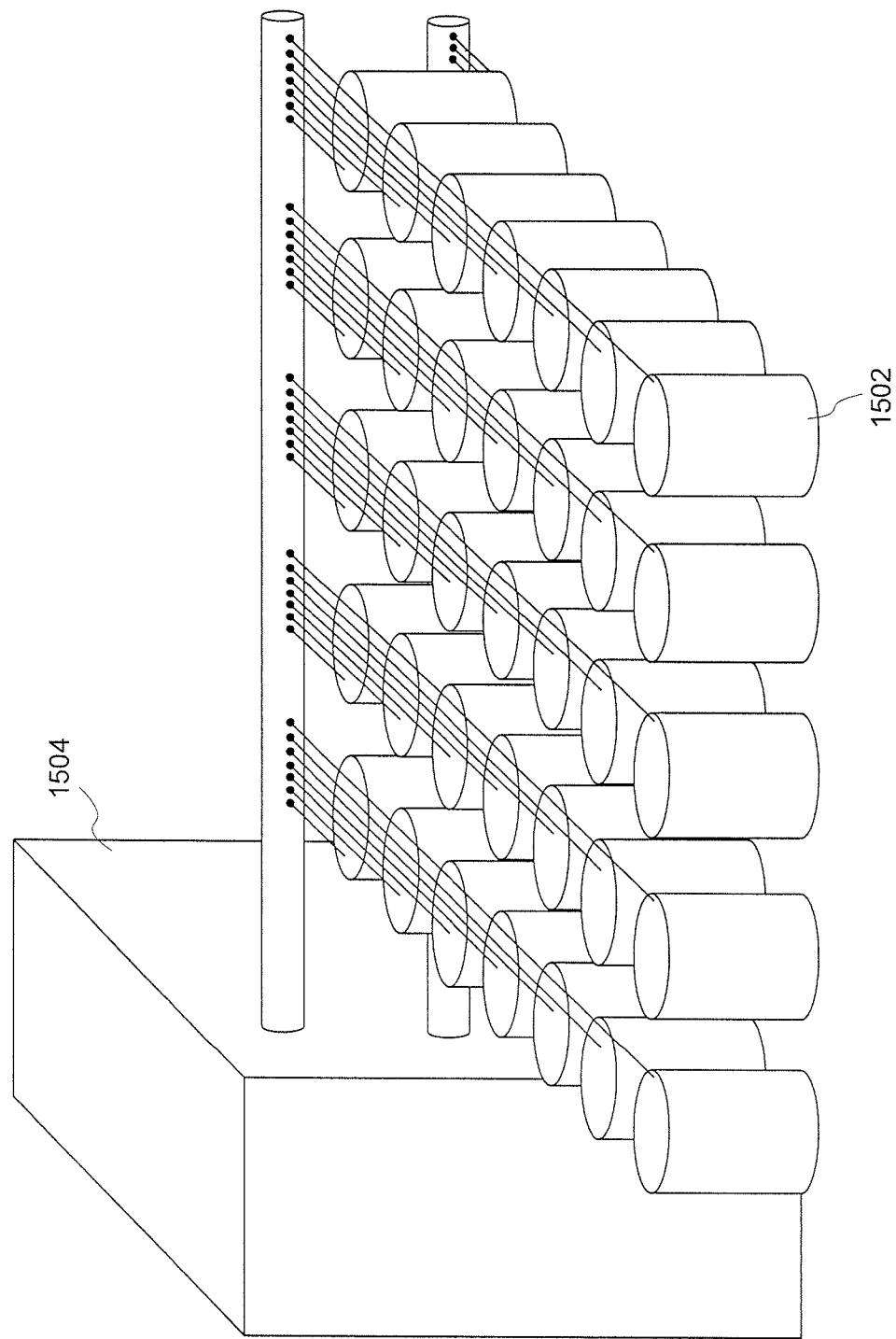
FIG. 15 illustrates, in one example, an array of cells that provides for parallel sequence determination.

FIG. 15 illustrates, in one example, an array of cells that provides for parallel sequence determination. Parallel sequence determination may be used to increase the sequence-determination throughput of the system. The array of cells includes multiple cells, such as cell 1502, and an analysis subsystem 1504 that processes and analyzes the voltage-signal outputs from the multiple cells in parallel. In general, the sequences output by a sequence-detection system may contain errors due to a variety of different operational error sources often present in the sequence-detection-system components, including the mechanical-change-sensor component, the mechanically coupled variable-resistance component, and the current or potential measuring circuitry. Therefore, depending on the level of accuracy desired, multiple identical targets may be sequenced and a consensus sequence may be computationally generated from the multiple sequences determined for the multiple identical targets. It is often the case that sequences for multiple targets are desired. In the array of cells illustrated in FIG. 15, each cell may be loaded with multiple copies of each of multiple different types of targets. The cells continuously produce sequence information from the multiple types of targets, with the targets processed in a nondeterministic order based on random association of primer-associated templates with the Klenow fragment of E. coli DNA polymerase I. The analysis subsystem 1502 continuously collects sequence information from multiple cells, such as cell 1504, assigns each sequence to a group of sequences generated by a particular target, and then compiles consensus sequences for each of the different types of target from the group of sequences obtained for each target type. Use of parallelism allows for rapid and efficient consensus-sequence determination for multiple targets.

Figure 16:
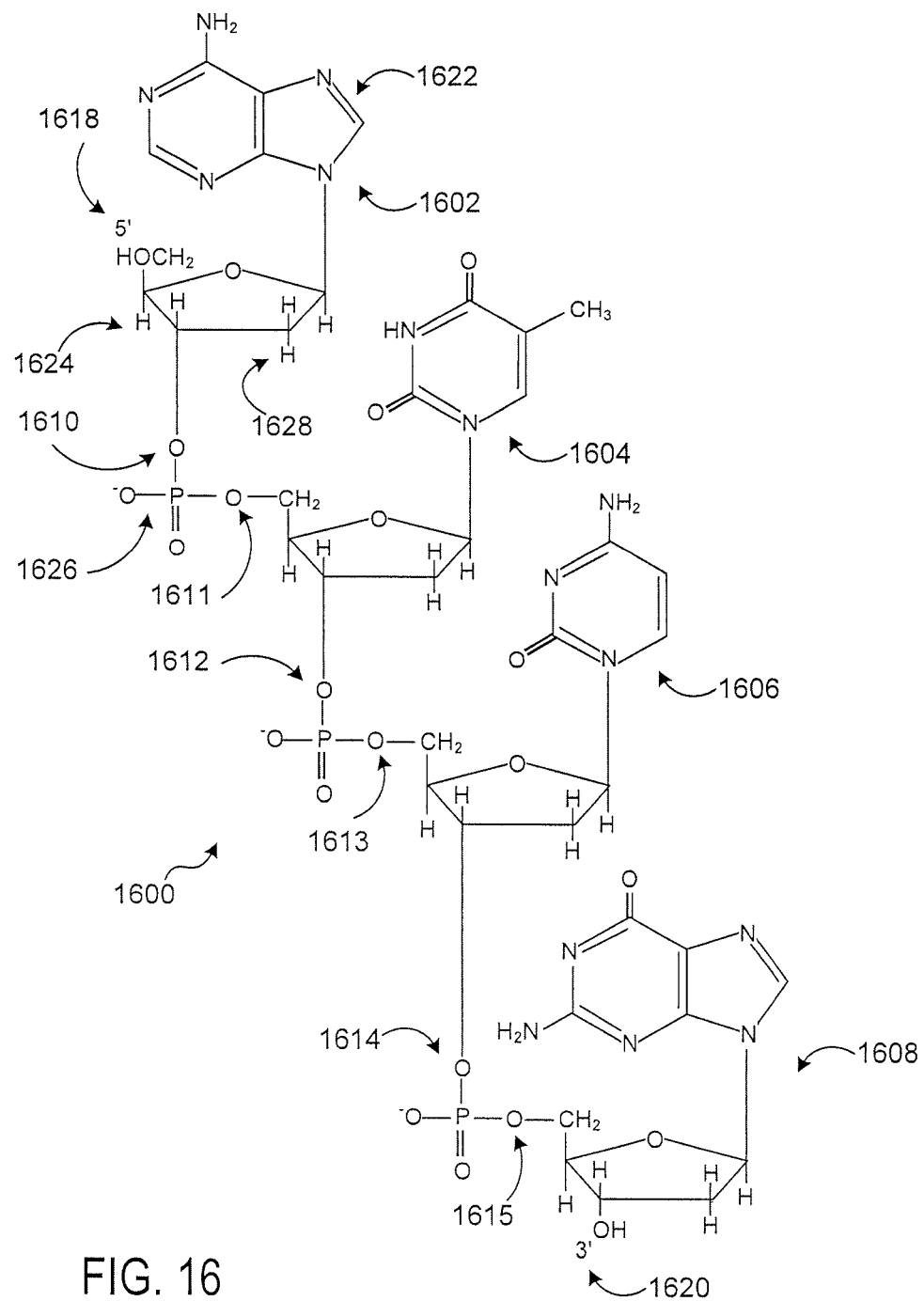
FIG. 16 illustrates a short DNA polymer.

FIGS. 16-19 illustrate deoxyribonucleic acids and peptides. FIG. 16 illustrates a short DNA polymer. Deoxyribonucleic acid ("DNA") is a linear polymer, synthesized from four different types of deoxy nucleotide triphosphates that, when incorporated within the polymer, are referred to as deoxynucleotide monomers. The deoxynucleotide monomers include: (1) deoxyadenylate, abbreviated "A," a purine-containing deoxynucleotide; (2) deoxythymididylate, abbreviated "T," a pyrimidine-containing deoxynucleotide; (3) deoxycytidylate, abbreviated "C," a pyrimidine-containing deoxynucleotide; and (4) deoxyguanidylate, abbreviated "G," a purine-containing deoxynucleotide. The corresponding nucleosides, which lack phosphate groups attached through phosphodiester bonds to ribose hydroxyl oxygens, are referred to as deoxyadenosine, deoxythymidine, deoxyctidine, and deoxyguanosine. FIG. 16 illustrates a short DNA polymer 1600, called an "oligomer" or "oligonucleotide," composed of the following subunits: (1) deoxyadenylate 1602; (2) deoxythymididylate 1604; (3) deoxycytidylate 1606; and (4) deoxyguanidylate 1608. The deoxynucleotide subunits are linked together through phosphodiester bonds 1610-1615 to form the DNA polymer. A linear DNA molecule, such as the oligomer shown in FIG. 16, has a 5' end 1618 and a 3' end 1620. Often, the 5' end 1618 includes a phosphate group linked to the 5' hydroxyl oxygen through a phosphoester bond. A DNA polymer can be chemically characterized by writing, in sequence from the 5' end to the 3' end, the single letter abbreviations for the deoxynucleotide subunits that together compose the DNA polymer. For example, the oligomer 1600 shown in FIG. 16 can be symbolically represented as "ATCG." A deoxynucleotide comprises a purine or pyrimidine base (e.g. adenine 1622 of the deoxyadenylate 1602), a deoxyribose sugar (e.g. deoxyribose 1624 of the deoxyadenylate 1602), and a phosphate group (e.g. phosphate 1626) that links one deoxynucleotide to another deoxynucleotide in the DNA polymer. Many non-natural nucleotides may be incorporated into DNA-like and RNA-like polynucleotides. Example modified nucleobases that can be included in a polynucleotide, whether having a native backbone or analogue structure, include, inosine, xathanine, hypoxanthine, isocytosine, isoguanine, 2-aminopurine, 5-methylcytosine, 5-hydroxymethyl cytosine, 2-aminoadenine, 6-methyl adenine, 6-methyl guanine, 2-propyl guanine, 2-propyl adenine, 2-thioLiracil, 2-thiothymine, 2-thiocytosine, 15-halouracil, 15-halocytosine, 5-propynyl uracil, 5-propynyl cytosine, 6-azo uracil, 6-azo cytosine, 6-azo thymine, 5-uracil, 4-thiouracil, 8-halo adenine or guanine, 8-amino adenine or guanine, 8-thiol adenine or guanine, 8-thioalkyl adenine or guanine, 8-hydroxyl adenine or guanine, 5-halo substituted uracil or cytosine, 7-methylguanine, 7-methyladenine, 8-azaguanine, 8-azaadenine, 7-deazaguanine, 7-deazaadenine, 3-deazaguanine, 3-deazaadenine or the like. Certain nucleotide analogues cannot become incorporated into a polynucleotide, for example, nucleotide analogues such as adenosine 5'-phosphosulfate.

The DNA polymers that contain the organization information for living organisms occur in the nuclei of cells in pairs, forming double-stranded DNA helixes. One polymer of the pair is laid out in a 5' to 3' direction, and is paired with a complementary polymer laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxyadenylate subunits of one strand hydrogen bond to deoxythymidylate subunits of the other strand and when deoxyguanylate subunits of one strand hydrogen bond to corresponding deoxycytidilate subunits of the other strand.

Figure 17A:
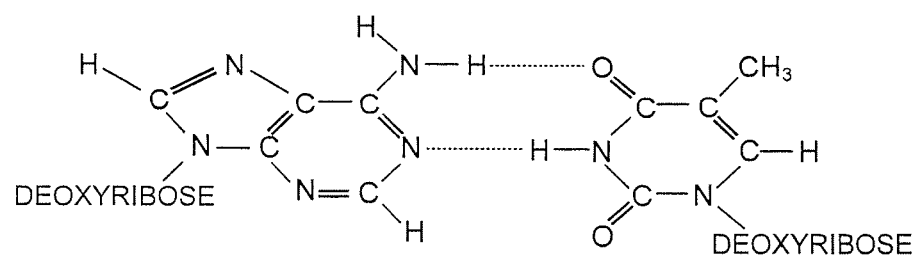
FIGS. 17A-17B illustrate the hydrogen bonding between the purine and pyrimidine bases of two anti-parallel DNA strands.
Figure 17B:
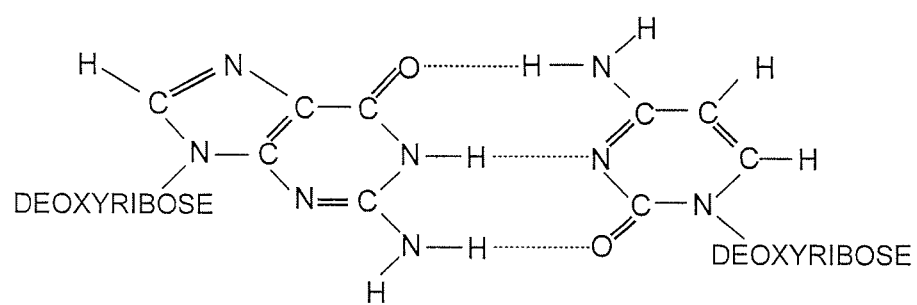

FIGS. 17A-17B illustrate the hydrogen bonding between the purine and pyrimidine bases of two anti-parallel DNA strands. FIG. 17A shows hydrogen bonding between adenine and thymine bases of corresponding deoxyadenylate and deoxythymididylate subunits and FIG. 17B shows hydrogen bonding between guanine and cytosine bases of corresponding deoxyguanidylate and deoxycytidylate subunits. Note that there are two hydrogen bonds 1002 and 1003 in the adenine/thymine base pair, and three hydrogen bonds 1004-1006 in the guanosine/cytosine base pair, as a result of which GC base pairs contribute greater thermodynamic stability to DNA duplexes than AT base pairs. AT and GC base pairs, illustrated in FIGS. 10A-B, are known as Watson-Crick ("WC") base pairs.

Figure 18B:
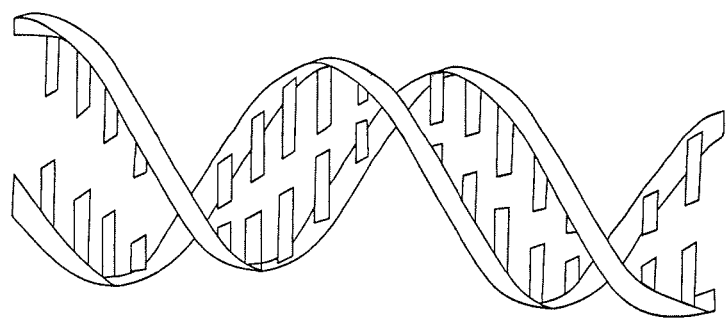
FIGS. 18A-18B illustrate double-stranded DNA.
Figure 18A:
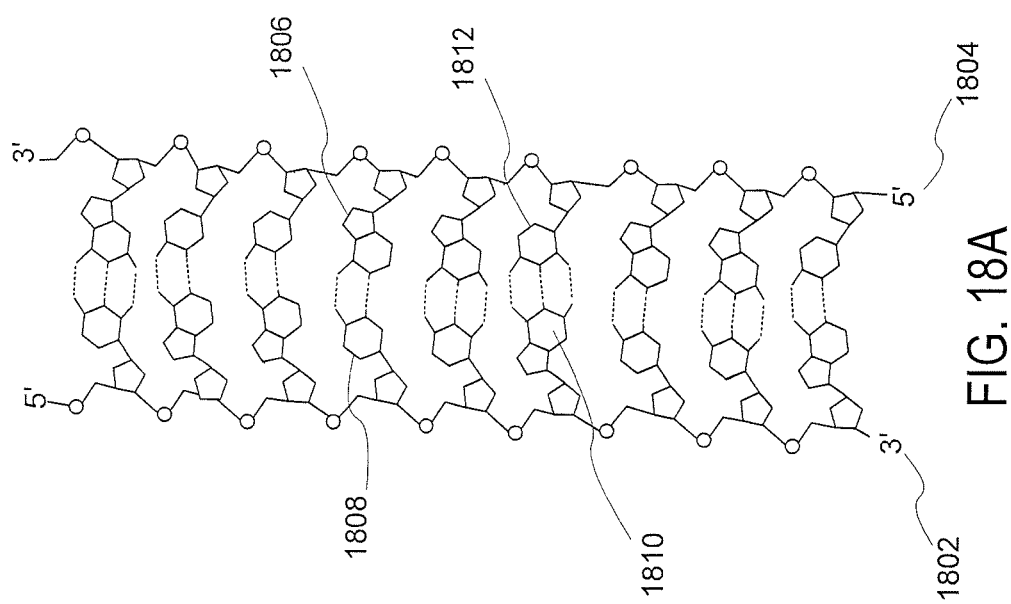

FIGS. 18A-18B illustrate double-stranded DNA. As shown in FIG. 18A, two strands of DNA polymer 1802 and 1804 with complementary sequences form an anti-parallel double-stranded complex through hydrogen bonds between complementary bases of the two strands. The double-strand complexes are antiparallel because the two strands have opposite 5'-3' orientations or polarities. An adenine base on one strand 1806 is paired with a thymine base 1808 of the other strand and a guanine base on one strand 1810 is paired with a cytosine base 1812 on the other strand. The sequence of deoxynucleotides in the 5'-3' direction along one strand is complementary to the sequence of deoxynucleotides in the 3'-5' direction along the other strand. The complementarity of the two strands within an anti-parallel double-stranded DNA polymer is produced when a DNA polymerase catalyzes the polymerization of a copy strand onto a template strand. FIG. 18B shows the familiar double-helix conformation of double-stranded DNA that occurs under physiological temperatures, pressures, pHs, and ion concentrations.

Figure 19:
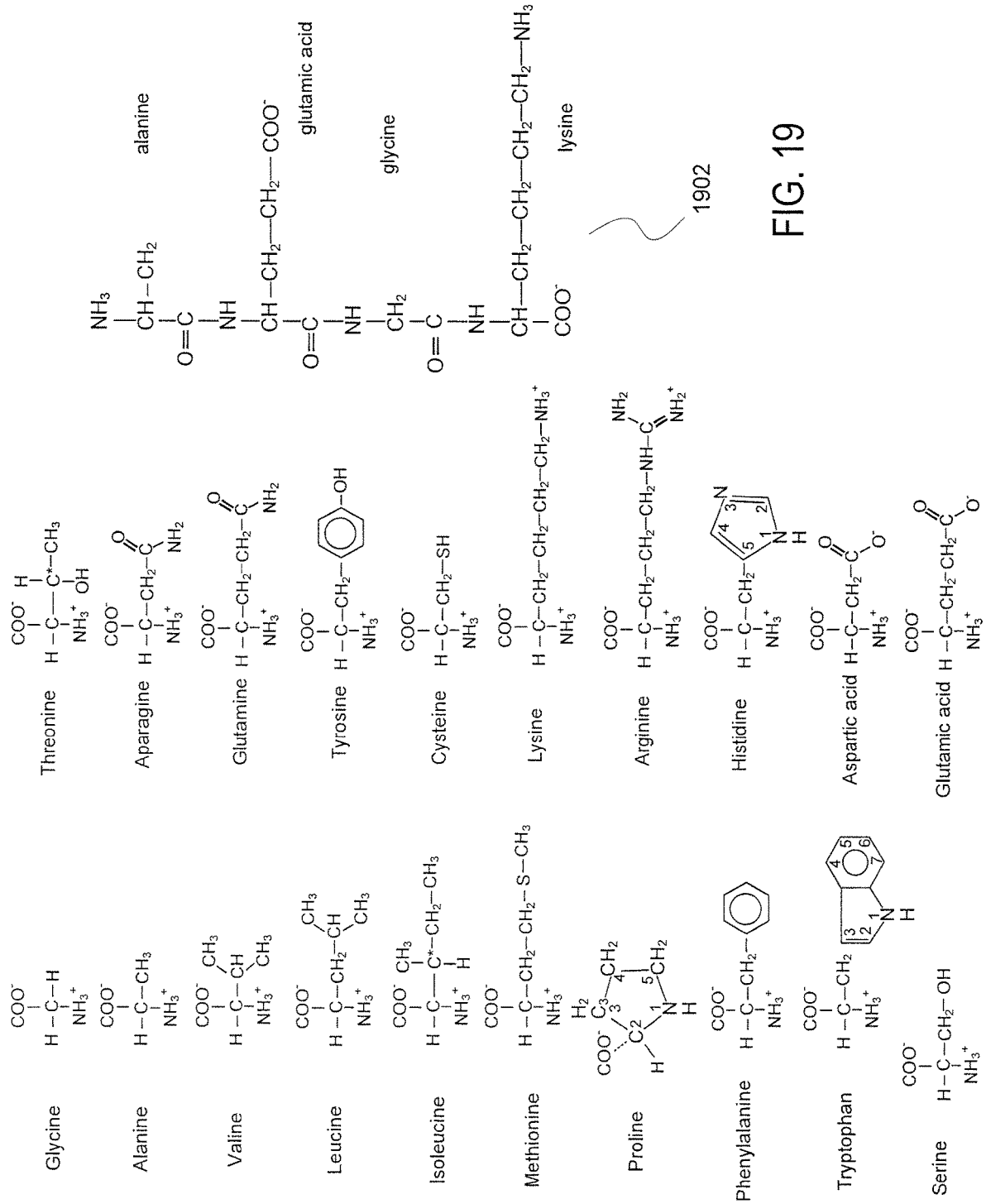
FIG. 19 shows the names and chemical structures of the 20 common amino acids.

FIG. 19 shows the names and chemical structures of the 20 common amino acids. Amino acids are polymerized in a ribosome-mediated translation process to form proteins. Amino acids are polymerized in a ribosome-mediated translation process to form proteins. FIG. 19 shows a short four-amino-acid polymer 1902, referred to as a "peptide," that includes alanine, glutamic acid-acid, glycine, and lysine monomers. Protein polymers commonly have hundreds to thousands of amino-acid monomers. Many proteins, such as the MspA porin, include multiple protein polymers. Under physiological conditions, proteins generally have complex three-dimensional conformations, such as the goblet-like conformation of the MspA porin octamer.

Figure 20:
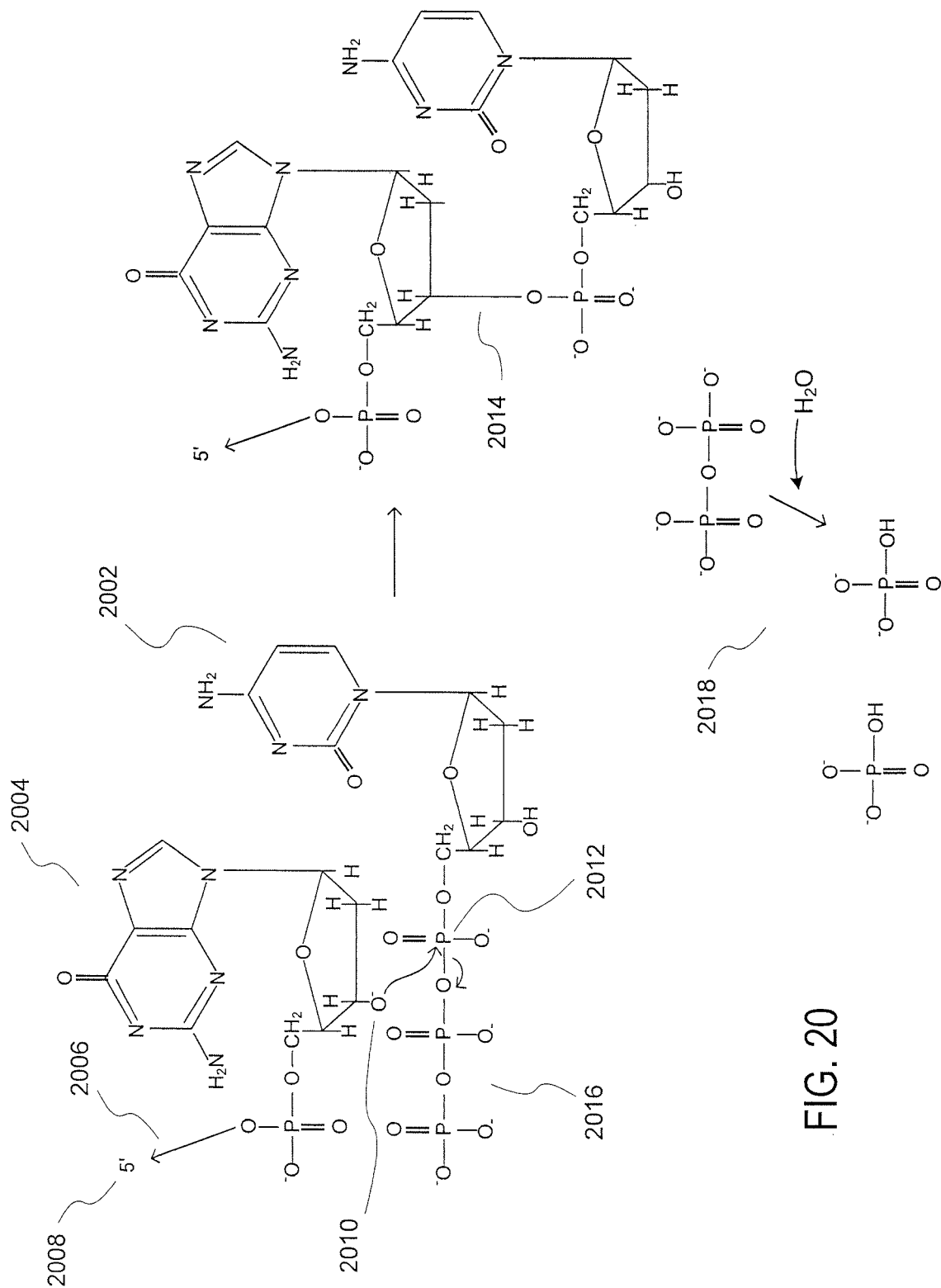
FIG. 20 illustrates the polymerization reaction catalyzed by the Klenow fragment of *E. coli* DNA polymerase I, used as the mechanical-change sensor component in the second sequence-detection system.

FIG. 20 illustrates the polymerization reaction catalyzed by the Klenow fragment of E. coli DNA polymerase I, used as the mechanical-change sensor component in the second sequence-detection system. This polymerization reaction adds a nucleotide triphosphate 2002 to the 3' end of a growing copy strand 2004. In FIG. 20, the remaining deoxynucleotide monomers in the copy strand are indicated by the arrow 2006 and the 5' label 2008. The deprotonated 3' hydroxyl 2010 of the 3'-terminal deoxynucleotide monomer in the copy strand carries out a nucleophilic attack on the α phosphate 2012 of the deoxynucleotide triphosphate 2002, forming a phosphodiester bond 2014 and displacing inorganic pyrophosphate 2016. This reaction has a relatively small change in free energy, under standard physiological conditions, but is driven by subsequent hydrolysis of the pyrophosphate 2018, which is accompanied by a large free-energy change. The chemical energy released by hydrolysis of the pyrophosphate not only drives the polymerization reaction, but also drives translation of the DNA polymerase relative to the primer-associated template strand and may contribute to the different dynamic conformations exhibited by the DNA polymerase when different deoxynucleotide triphosphates are specifically associated with the active site and hydrogen bond with complementary deoxynucleotide monomers in the template strand.

FIGS. 21A-21E illustrate copy-strand extension catalyzed by the Klenow fragment of E. coli DNA polymerase I. FIGS. 21A-E all use the same illustration conventions, next described with reference to FIG. 21A. The DNA polymerase is represented by a sphere 2102, which appears as a circle in cross-section. The active site within the DNA polymerase is represented by a vertically oriented, shaded rectangle 2104. The template DNA strand 2106 and the copy DNA strand 2108 are represented by a series of rectangles and discs. The purine and pyrimidine bases are represented by long, vertically oriented, labeled rectangles, such as rectangle 2110, which represents a guanine base. The ribose moiety within each deoxynucleotide monomer is represented by a small square, such as small square 2112. The phosphodiester bonds joining to deoxynucleotide monomers within a strand are represented by circles, such as circle 2114. Curved arrows, such as curved arrow 2116, indicate that the strands continue in the indicated directions.

Figure 21A:
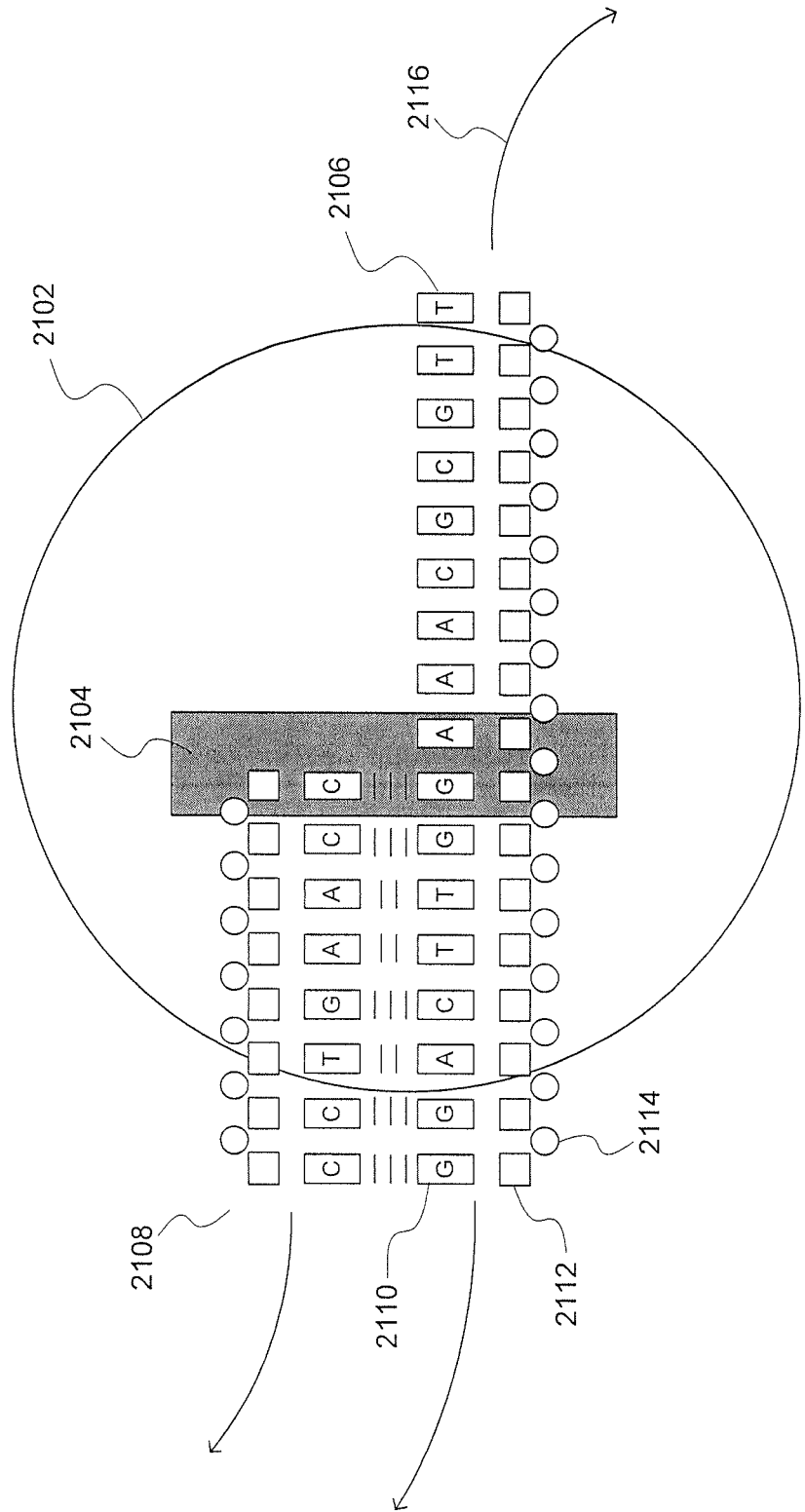
FIGS. 21A-21E illustrate copy-strand extension catalyzed by the Klenow fragment of *E. coli* DNA polymerase I.
Figure 21B:
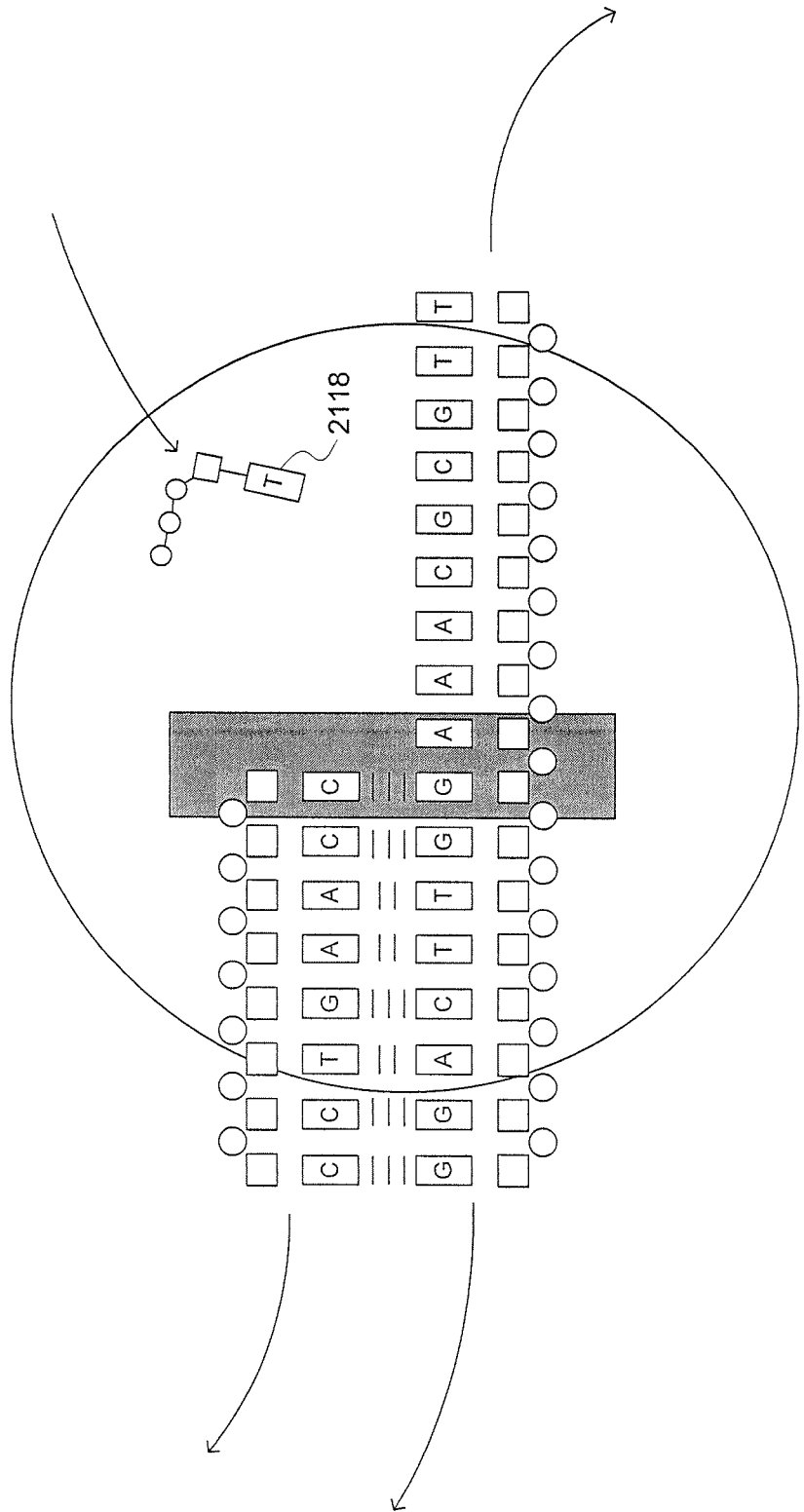
Figure 21C:
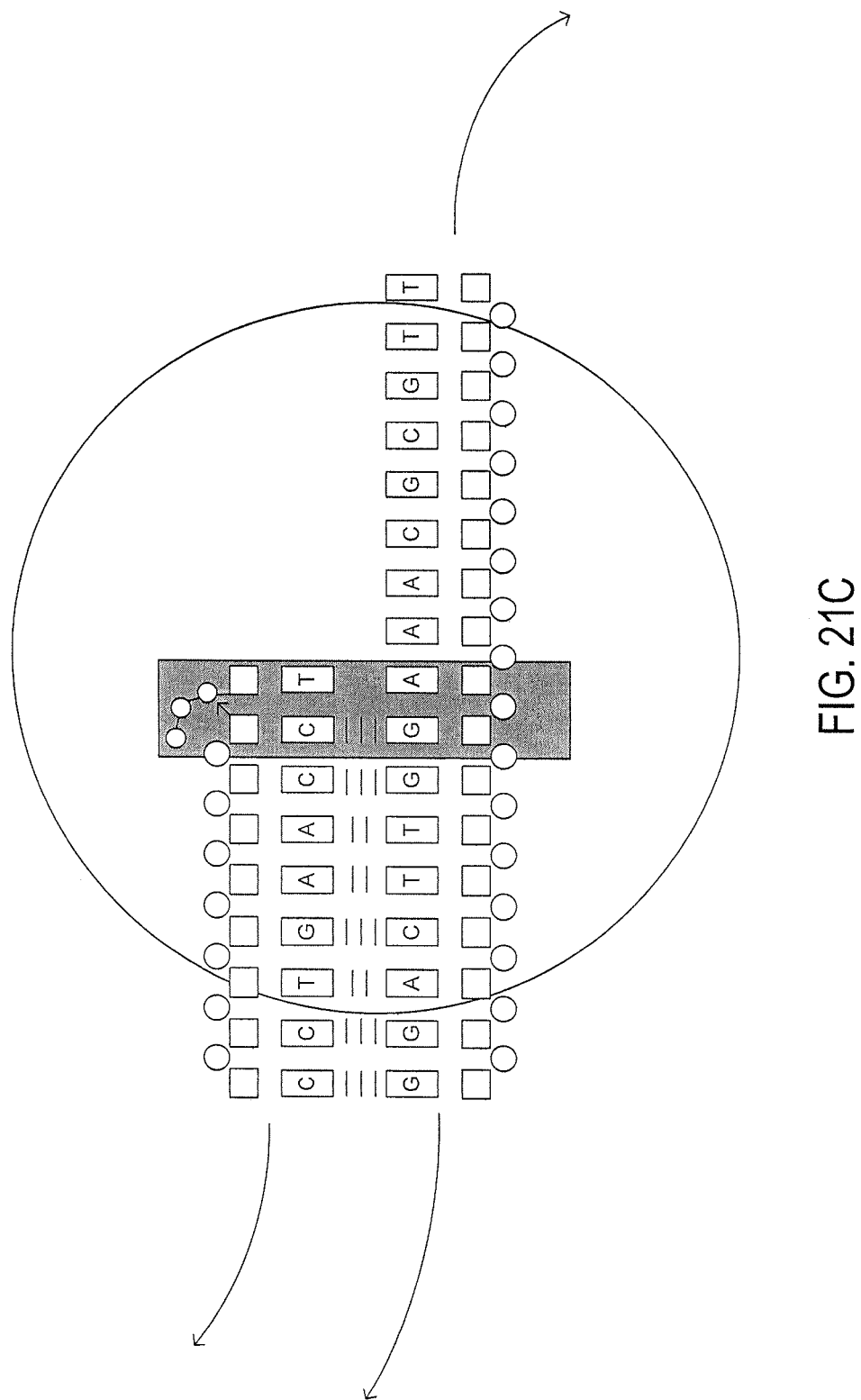

FIG. 21A shows the DNA polymerase without a deoxynucleotide triphosphate occupying the active site. The DNA polymerase is ready to receive a next deoxynucleotide triphosphate for addition to the 3' end of the copy strand. The active site of the DNA polymerase is a complex chemical environment that includes several bound magnesium ions and numerous functional groups of amino-acid-monomer sidechains that all contribute to specific binding of the template and copy strands, to specific binding of a deoxynucleotide triphosphate for addition to the 3' end of the copy strand via the reaction illustrated in FIG. 20, and to catalysis of the polymerization reaction, including stabilization of one or more transition states. In FIG. 21B, a deoxynucleotide triphosphate diffuses through channels in the DNA polymerase towards the active site. In at least one example, any of the four different types of deoxynucleotide triphosphate may approach the active site, but only a deoxynucleotide triphosphate that is complementary to the unpaired deoxynucleotide monomer of the template strand within the active site is stably associated with the active site for hydrogen bonding with the unpaired active-site-resident template-strand deoxynucleotide monomer, as shown in FIG. 21C. Stable association of the deoxynucleotide triphosphate with the active site is associated with a conformational change in the DNA polymerase, represented by an ellipsoid shape in FIG. 21C. The actual conformational changes are complex, affecting multiple different domains within the DNA polymerase. The DNA-polymerase conformation is dynamic, and is generally associated with various types of subtle oscillation modes and relative motions of various structural domains. The specific association of each different type of deoxynucleotide triphosphate with the active site induces a different dynamical DNA-polymerase conformation, a change in the relative positions or orientations of the DNA-polymerase and porin, and/or other changes which are thought to be the source of the mechanical-change mechanical signal generated by the DNA polymerase acting as the mechanical-change sensor component of the second sequence-detection system.

Figure 21D:
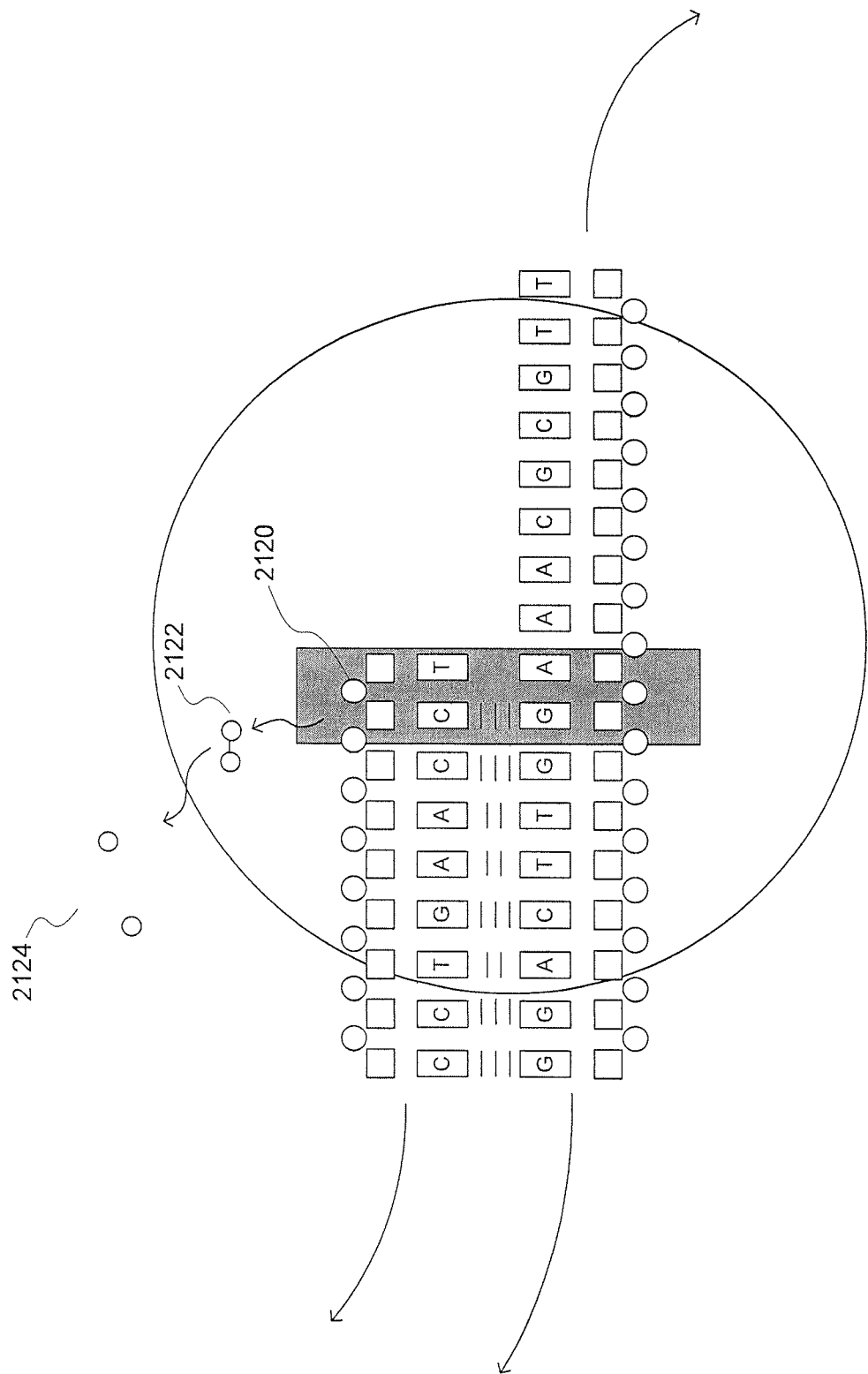
Figure 21E:
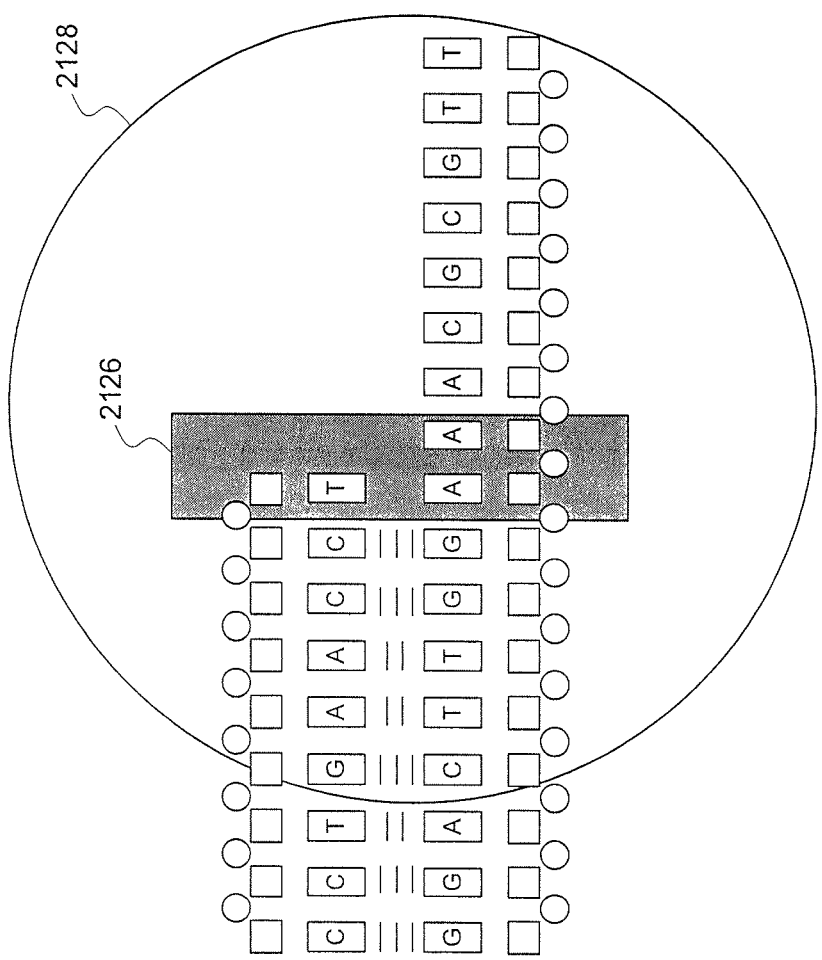

In the sequence of figures that includes FIGS. 21C-21D, the polymerization reaction illustrated in FIG. 20 occurs, forming the phosphodiester-bond bridge 2120 that incorporates the new deoxynucleotide monomer into the copy strand. The pyrophosphate 2122 is released from the active site. In the sequence of figures that includes FIGS. 21C-21E, the DNA polymerase translates relative to the template and copy strands to again form an active site 2126 without a nucleotide triphosphate, ready for specific incorporation of a subsequent deoxynucleotide triphosphate. Note that the conformation of the DNA polymerase has reverted to the original conformation, represented in FIG. 21E by a spherical shape 2128. It should be noted that, in certain implementations, specific association of deoxynucleotide monomers with the active site, alone, without incorporation, can still lead to mechanical changes of the polymerase that can be transduced into a signal from which the target sequence can be determined. Incorporation of nucleotides into a copy strand is not necessary in these implementations.

Figures 22A, 22B:
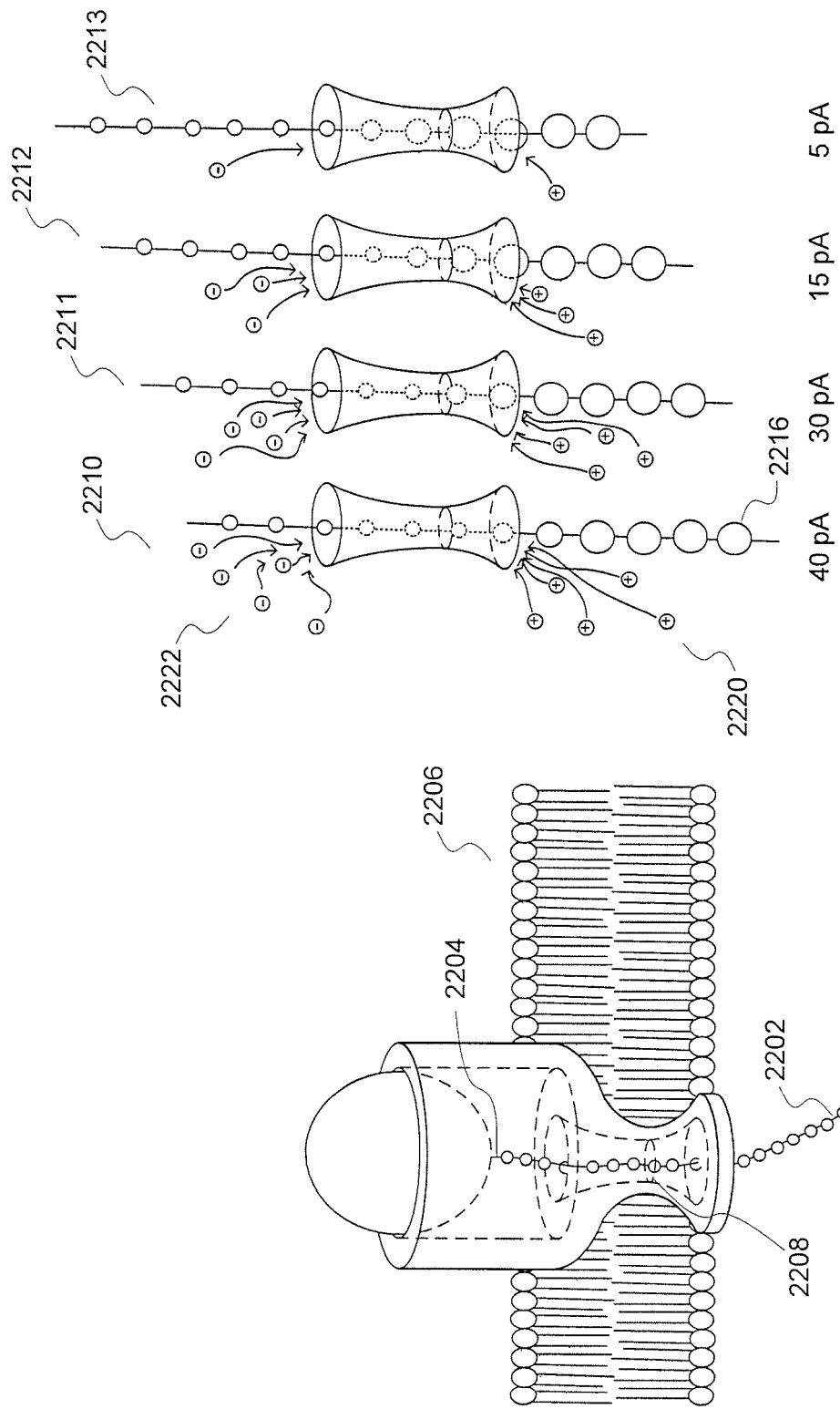
FIGS. 22A-22B illustrate, in one example, the variable-resistance component of the second sequence-detection system.

FIGS. 22A-22B illustrate, in one example, the variable-resistance component of the second sequence-detection system. As shown in FIG. 22A, the DNA-polymer tether 2202 is attached to the DNA polymerase 2204 and extends through the porin channel into the second solution-containing chamber 1310 of the cell below the lipid bilayer 2206. As the deoxynucleotide triphosphates are specifically associated with the active site of the DNA polymerase during copy-strand extension, changes in the dynamical conformation of the DNA polymerase result in translation of the DNA-polymer tether relative to a narrow construction 2208 in the porin channel.

FIG. 22B illustrates how translation of the DNA-polymer tether with respect to the narrow constriction in the porin channel leads to varying resistance to ion flow through the porin channel. FIG. 22B shows four different positions of a DNA-polymer tether within the porin channel 2210-2213. The DNA-polymer tether is represented as a series of circles with different diameters. Large-diameter circles, such as circle 2216, represent one or more deoxynucleotide monomers that impart high resistance to ion flow through the porin channel when positioned within the narrow constriction 2218 of the born channel. Circles with increasingly smaller diameters represent one or more deoxynucleotide monomers that impart increasingly less resistance to ion flow through the porin channel when positioned within the narrow constriction. In the first position 2210, one or more a low-resistance deoxynucleotide monomers are positioned within the narrow constriction 2218, as a result of which there is relatively high rate of ion-current flow through the porin channel, as represented by the large number of positive 2220 and negative 2222 ion symbols shown entering the porin channel. As the DNA-polymer tether moves upward relative to the narrow constriction, in positions 2211-2213, one or more deoxynucleotide monomers that impart increasingly greater resistance to ion flow move into the narrow constriction, resulting in increasingly smaller rate of ion-current flow through the porin channel. Thus, positioning of the DNA-polymer tether within the porin channel varies the resistance to ion flow through the porin channel and transduces the mechanical mechanical-change signal generated by specific incorporation of deoxynucleotide triphosphates into the active side of the DNA polymerase into an electrical signal that is transduced, by the current-to-voltage-converter circuitry discussed above with reference to FIGS. 14A-14B, into an output voltage signal.

Figure 23:
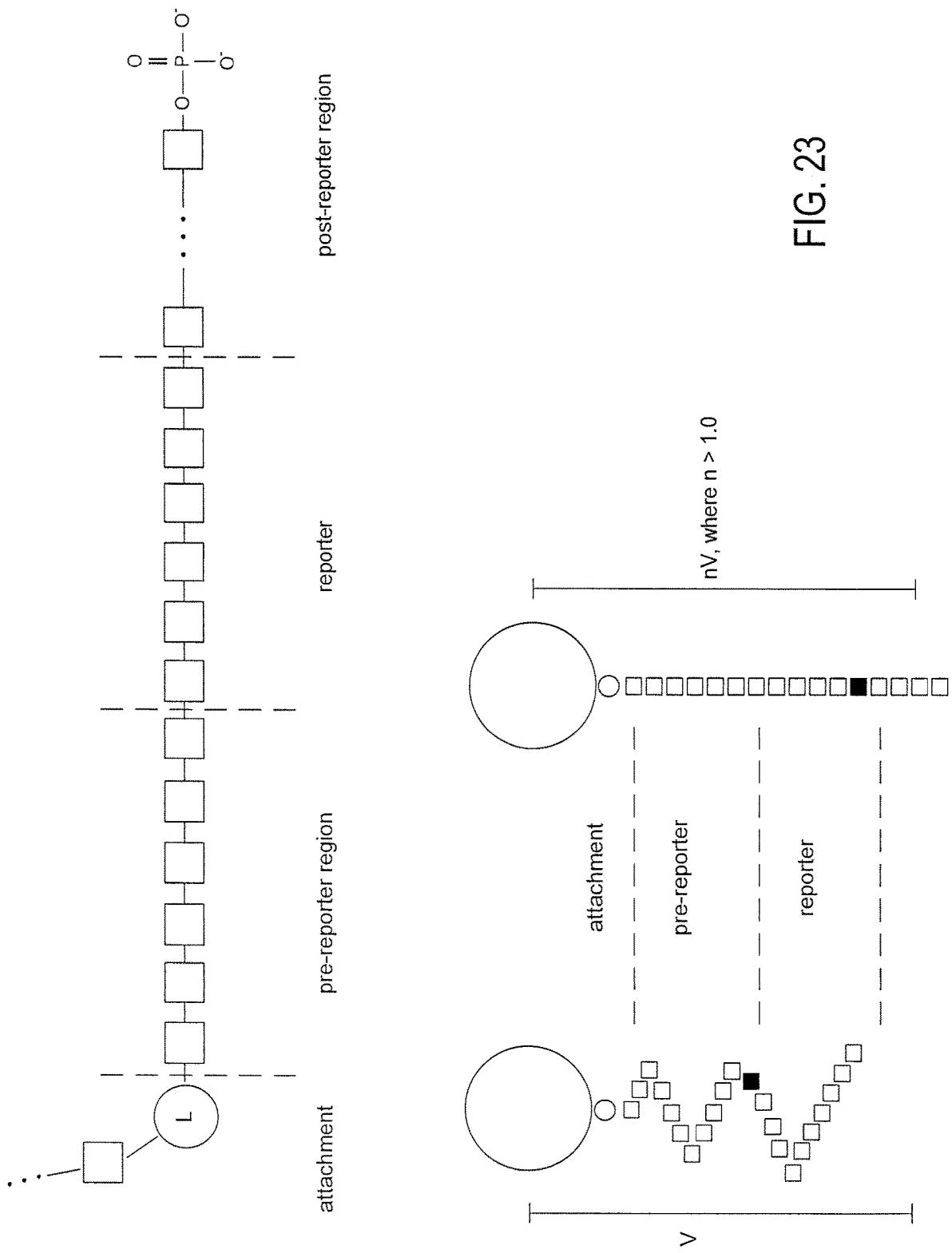
FIG. 23 illustrates, in one example, several features of the DNA-polymer tether that mechanically couples the DNA polymerase to the variable-resistance component and that additionally forms a portion of the variable-resistance component.

Calibration and Tuning of the Second Type of Shape-Change-Based Sequence Detector FIG. 23 illustrates, in one example, several features of the DNA-polymer tether that mechanically couples the DNA polymerase to the variable-resistance component and that additionally forms a portion of the variable-resistance component. The DNA-polymer tether 2302 includes, in certain implementations, a linker 2304 through which the DNA-polymer tether is attached to the DNA polymerase, a pre-reporter region 2306 that includes, in certain implementations, approximately six deoxynucleotide monomers, a reporter region 2308 that generally includes at least four deoxynucleotide monomers, and a post-reporter region that may include from several to many tens of deoxynucleotide monomers 2310. The reporter region 2308 is the region that lies within the narrow constriction within the porin channel when the DNA polymerase exhibits the various different conformations that together comprise the shape changes exhibited by the shape change sensor component of the second sequence-detection system. The lengths of the various DNA-polymer-tether regions may vary with different implementations that use different porins and/or different DNA polymerases. The regions are defined by the distance between the attachment point of the DNA-polymer tether to the DNA polymerase and the narrow constriction in the porin channel as well as the range of displacements in the position of the DNA-polymer tether induced by conformational changes of the DNA-polymerase.

As shown in the lower portion of FIG. 23, the DNA-polymer tether generally has a certain amount of dimensional flexibility. When a relatively low voltage is applied to the cell 2312, the DNA-polymer tether may inhabit any of various relaxed states 2314 while, when voltages of higher magnitudes are applied to the cell 2316, the DNA-polymer tether inhabits one of various stretched or taut states 2318. A given deoxynucleotide monomer 2320 may lie at the boundary of the pre-reporter and reporter regions, in the relaxed state, but, in the stretched or taut state, the same deoxynucleotide monomer may lie well within the reporter region. By varying the applied voltage to the cell, relatively fine-grain adjustments are made to the resting or baseline position of the DNA-tether and, specifically, to the resting or baseline position of the reporter region relative to the constriction in the porin channel. This provides a means for calibrating the cell with respect to the output-voltage magnitude and with respect to the mechanical-to-electrical-signal-transduction responsiveness of the cell.

Different sequences of deoxynucleotide monomers within the reporter region provide different resistances to ion-current flow through the porin channel. Various experiments with DNA-polymer tethers having different reporter-region deoxynucleotide-monomer sequences have led to the identification of a number of low-current, high-resistance reporter-region sequences and a number of high-current, low-resistance reporter-region sequences. The varying-resistance profile of the variable-resistance component with respect to mechanical translation of the DNA-polymer tether within the porin channel can be precisely designed by varying the deoxynucleotide-monomer sequence of the reporter region.

Figure 24:
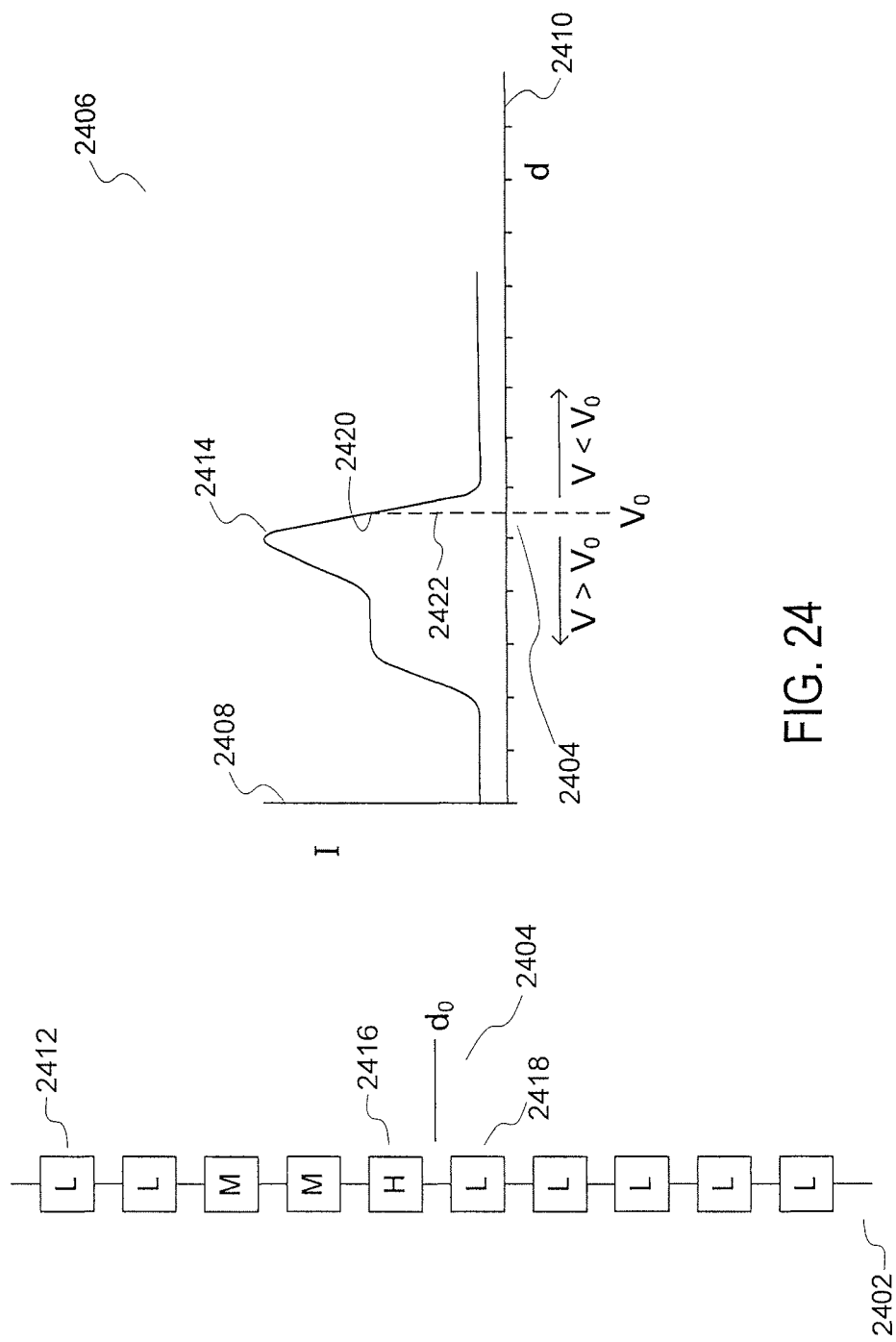
FIG. 24 illustrates, in one example, tuning the signal response of the cell.

FIG. 24 illustrates, in one example, tuning the signal response of the cell. The DNA-polymerase mechanical-change component may occupy different positions relative to porin channel and may adopt different conformations under different conditions and cell-parameter values, as a result of which the position of the reporter region relative to the porin constriction may vary. A hypothetical reporter-region 2404 is shown on the left-hand side of FIG. 24. As discussed above, the reporter region moves up and down within the porin channel. The movements are characterized as displacements in negative, or upward, displacements and positive, or downward, displacements from a reference displacement 2404 considered to have the value 0, $d_0$. A plot 2406 of the signal strength, or voltage magnitude of the output signal, with respect to reporter displacement is shown on the right-hand side of FIG. 24. The vertical axis 2408 represents the rate of current flow through the porin channel, or magnitude of the output voltage signal, and the horizontal axis 2410 represents the displacement of the reporter within the porin channel relative to the reference displacement $d_0$. The reporter region 2402 is represented by a series of labeled squares, such as square 2412. Each square represents a single deoxynucleotide monomer or a short sequence of deoxynucleotide monomers. The letter "L" stands for low-current, the letter "M" stands for medium-current, and the letter "H" stands for high-current. The current-signal curve 2414 mirrors the current-flow indications in the representation of the reporter region 2402 and inversely mirrors the resistivities of the deoxynucleotide monomers or short sequences of deoxynucleotide monomers represented by the small squares in the representation of the reporter region 2402. In other words, were the reporter-region representation rotated by 90° in a counter-clockwise direction and superimposed with the horizontal axis 2410 of plot 2406, the current-flow indications for each of the deoxynucleotide monomers or sets of deoxynucleotide monomers and their positions along the displacement axis could be used as vertical and horizontal coordinates for placing points in the plot that, when connected together by a continuous curve, would produce the current-signal curve 2414 shown in plot 2406. The steepest portion 2420 of the current-signal curve 2414 is bisected, as indicated by vertical dashed line 2422 in FIG. 24, at the point with displacement coordinate equal to $d_0$. In general, this reference position would provide the greatest sensitivity in the voltage-signal output by the cell to changes in the conformation of the DNA-polymerase mechanical-change sensor component, and is thus represents the desirable resting point, or baseline point, for the reporter within the porin channel. Because the reporter and the porin channel are nanoscale components, it would be difficult to mechanically configure the cell so that the reporter would be disposed within the porin channel at the desired reference-displacement position. However, as discussed above with reference to FIG. 23, varying the voltage applied to the cell allows for fine-grained adjustment in the baseline, or resting, position of the reporter within the porin channel. Since the shape and form of the current-signal curve 2414 is determined by the sequence of deoxynucleotide monomers within the reporter region, the response of the cell can be initially calibrated by varying the applied voltage to the cell in order to position the reporter region at the desired reference displacement, bisecting the steepest portion of the current-signal curve. Thus, the current-flow response to reporter-region displacement due to conformational changes in the DNA polymerase can be precisely tailored through careful design of the deoxynucleotide sequence within the DNA-polymer-tether reporter region and the current-flow response can be calibrated by varying the voltage applied to the cell.

Figure 25:
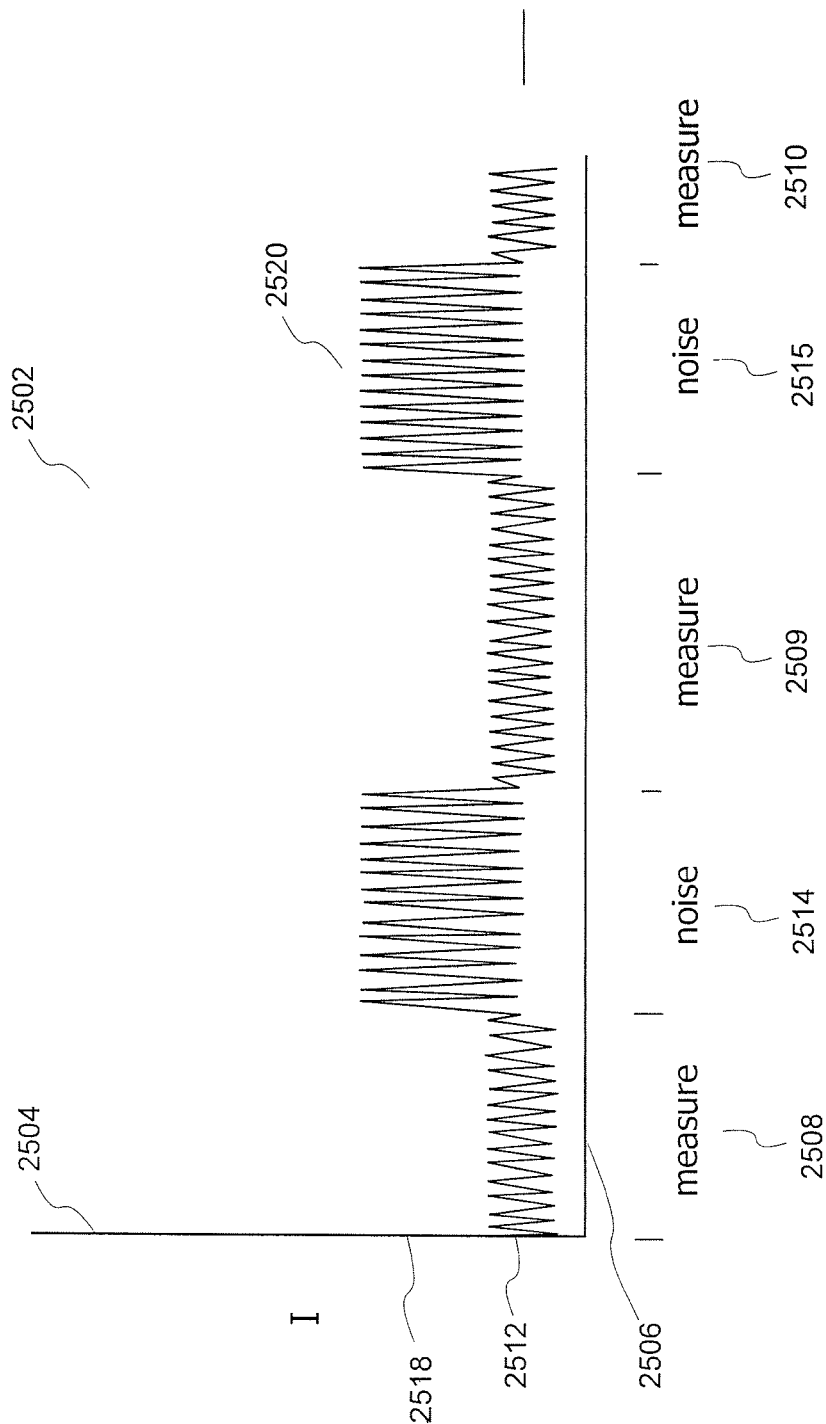
FIG. 25 illustrates, in one example, the periodic occurrence of noise within the second type of sequence-detection system when a Klenow-fragment of *E. coli* DNA polymerase I is used as the shape-change sensor component.

FIG. 25 illustrates, in one example, the periodic occurrence of noise within the second type of sequence-detection system when a Klenow-fragment of *E. coli* DNA polymerase I is used as the mechanical-change sensor component. This type of noise has been observed when alternative DNA-polymerase mechanical-change sensors are used in the second type of sequence-detection system. FIG. 25 shows a plot 2502 of the current signal, represented by the vertical axis 2504, with respect to time, represented by the horizontal axis 2506. For certain periods of time 2508-2510, the average current flow has a relatively low value 2512. However, during other periods of time 2514 and 2515, the average current flow has a significantly higher value 2518. In addition, the range of displacements to the average current flow in the low-current-flow periods 2508-2510 is much smaller than the range of displacements to the average current flow in the high-current-flow periods 2514 and 2515. The data-containing current-signal curves are superimposed over the noisy signal 2520 shown in FIG. 25. The data-containing current-signal curves are readily extracted from the current signal output during the low-noise, low-current-flow periods 2508-2510, but cannot be extracted from the noisy current signal output during the high-current-flow periods 2514 and 2515, since the noise essentially masks the relatively smaller information-carrying current fluctuations. The low-noise, low-current-flow periods 2508-2510 are labeled "measure" in FIG. 25, while the high-current-flow periods 2514 and 2515 are labeled "noise." When steps are not taken to reduce or eliminate the noisy periods, large amounts of sequence information are lost, since copy-strand elongation by the DNA-polymerase mechanical-change sensor component may continue during the noisy periods, when the output-voltage changes corresponding to changes in conformation of the DNA-polymerase mechanical-change sensor component cannot be extracted from the output-voltage signal. Even disregarding the loss of sequence information, the periods of sequence-information-masking noise represent a significant decrease in the rate of sequence-information acquisition. However, as discussed further below, the periods of sequence-information-masking noise provide a benefit in that the sequence-information-masking noise occurs only when the DNA-polymer tether is threaded through the porin channel and when the DNA polymerase is associated with the porin, and thus provides an indication that the mechanical-change sensor component and variable-resistance components are initially configured.

Figure 26:
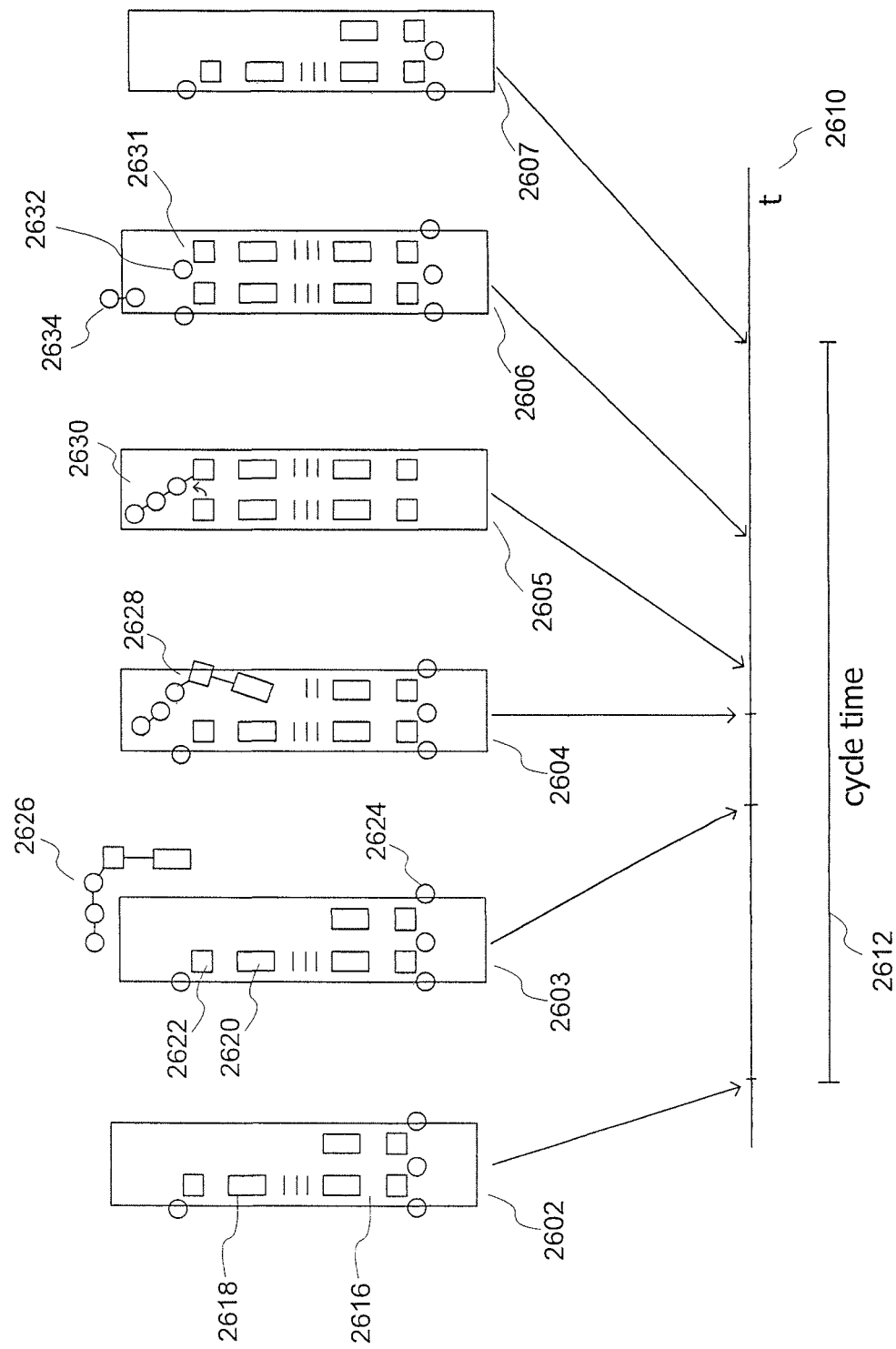
FIG. 26 illustrates copy-strand extension catalyzed by the Klenow fragment of *E. coli* DNA polymerase I.

FIG. 26 illustrates copy-strand extension catalyzed by the Klenow fragment of *E. coli* DNA polymerase I. The active site within the DNA polymerase is represented, at various time points during incorporation of a nucleotide triphosphate into the copy DNA strand, by vertically oriented rectangles 2602-2607. The time points depicted by these active-site representations are indicated along a timeline 2610. One full cycle of nucleotide-triphosphate incorporation spans the time segment 2612 shown below the timeline. FIG. 26 uses the same illustration conventions used in FIGS. 21A-E. Hydrogen bonds are represented, as in FIGS. 21A-E, but, since the identities of the base-paired nucleotides are not identified or relevant, three short horizontal line segments are used to generically represent hydrogen bonds, whether two hydrogen bonds for AT base pairs or three hydrogen bonds between GC base pairs. Portions of the template DNA strand 2616 and the copy DNA strand 2618 are represented by rectangles and discs. The purine and pyrimidine bases are represented by long, vertically oriented rectangles, such as rectangle 2620. The ribose moiety within each deoxynucleotide monomer is represented by a small square, such as small square 2622. The phosphodiester bonds joining two deoxynucleotide monomers within a strand are represented by circles, such as circle 2624.

Initially, the active site 2602 is ready to receive a next deoxynucleotide triphosphate for addition to the 3' end of the copy DNA strand 2618. Next, a deoxynucleotide triphosphate 2626 approaches the active site. Of course, any of the four different types of deoxynucleotide triphosphate may approach the active site, but the affinity of a deoxynucleotide triphosphate for the active site that is complementary to the unpaired deoxynucleotide monomer of the template strand within the active site is generally greater than the binding affinities of non-complementary deoxynucleotide triphosphates, and the complementary deoxynucleotide triphosphate is most likely to specifically associate with the active site 2628 for hydrogen bonding with the unpaired active-site-resident template-strand deoxynucleotide monomer. This time required for specific association of a next nucleotide triphosphate with the active site is influenced by many cell parameters, including the concentrations and types of nucleotide triphosphates in the cell-chamber solution and the temperature. Next, the polymerization reaction 2630-2631 illustrated in FIG. 20 occurs, forming the phosphodiester-bond bridge 2632 that incorporates the new deoxynucleotide monomer into the copy strand. The time required for this reaction is influenced by many cell parameters, including, for example, the type of nucleotide triphosphates in the cell-chamber solution, the temperature, the concentration of magnesium ions in the cell-chamber solution, the pH of the cell-chamber solution, and the types and concentrations of other ionized salts in the cell-chamber solution. Inorganic pyrophosphate 2634 is released from the active site. The DNA polymerase translates relative to the template and copy DNA strands to again form an active site 2607 without a nucleotide triphosphate, ready for specific association of a subsequent deoxynucleotide triphosphate. This translation is influenced by various cell parameters, including, as one example, temperature.

The length of the nucleotide-triphosphate-addition cycle, represented by line segment 2612, is a significant parameter with respect to operation of the second type of sequence-detection system. In order for reliable data to be extracted from the output voltage signal by the analysis subsystem, the conformational changes in the DNA-polymerase mechanical-change sensor component need to occur over a sufficiently long period of time to allow the current-to-voltage-converter data-sampling circuitry to detect the conformational changes in corresponding current-flow changes and to produce a current signal that includes sufficient information to allow the type of nucleotide triphosphate to be determined by signal processing within the analysis subsystem. However, the speed of sequence determination is directly proportional to the rate at which nucleotide triphosphate are incorporated into the copy DNA strand. As discussed below, there are many different adjustable parameters associated with the second type of sequence-detection system that can be tuned to provide a desirable nucleotide-triphosphate-addition-cycle length that is sufficiently long to ensure accurate DNA-template-sequence determination but that is sufficiently short to ensure that a desired rate of sequence determination is achieved.

Figure 27:
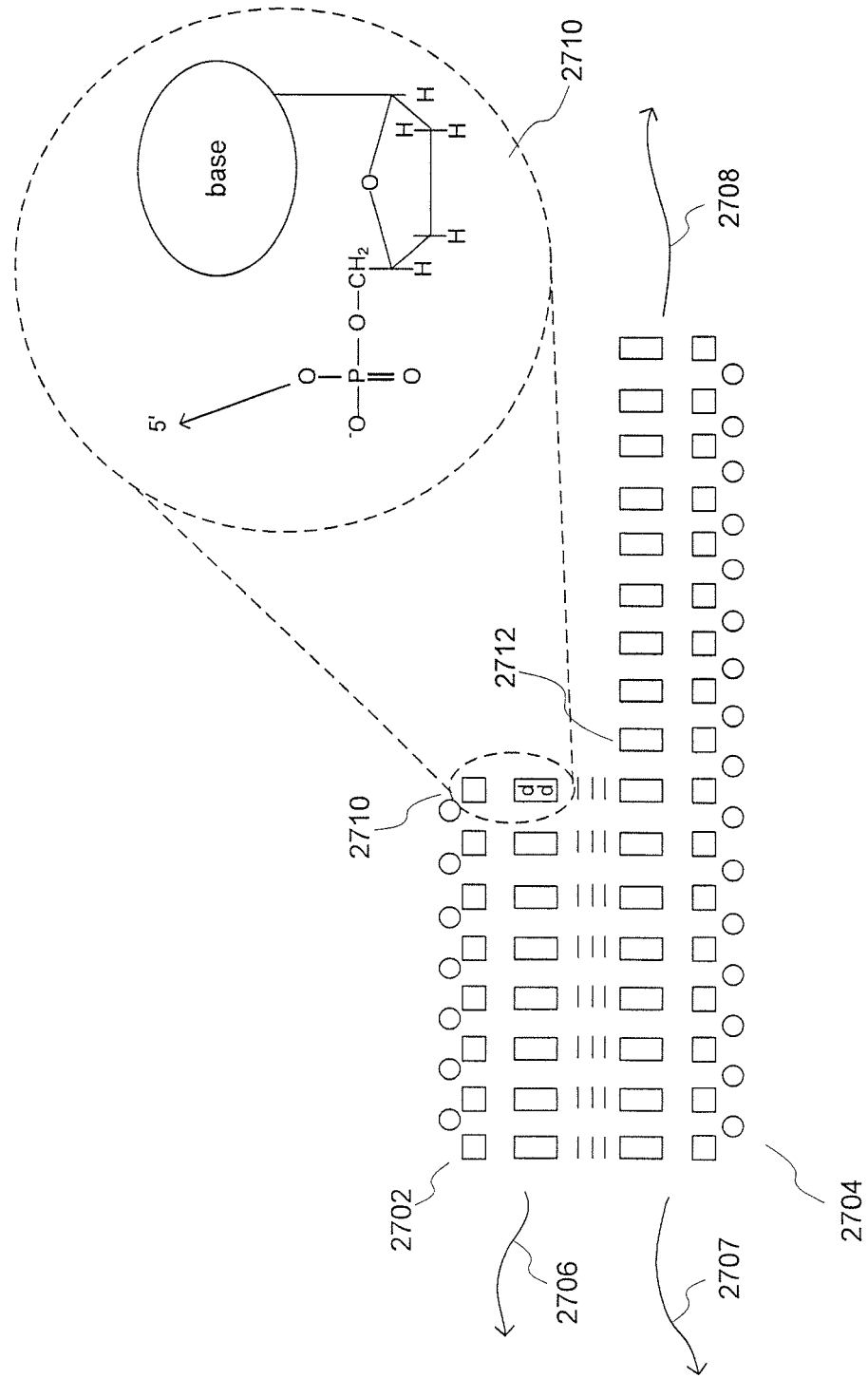
FIG. 27 illustrates, in one example, a primer-associated template DNA strand configured for single-position deoxynucleotide-monomer-type determination.

In certain implementations, it is desirable to configure the second type of sequence-detection system to determine only the type of deoxynucleotide monomer at a particular single position within the DNA template. FIG. 27 illustrates, in one example, a primer-associated template DNA strand configured for single-position deoxynucleotide-monomer-type determination. FIG. 27 uses the same illustration conventions used in FIG. 26 to represent the primer DNA 2702 and the primer-associated template DNA strand 2704. In the case of certain DNA polymerases, an RNA primer may be used in place of a DNA primer. In either case, the primer may include a dideoxynucleotide monomer 2710 at the 3' end. The dideoxynucleotide monomer lacks a 3' hydroxyl and therefore cannot be elongated by addition of nucleotide triphosphates by the nucleotide-triphosphate-addition reaction discussed above with reference to FIG. 20. However, a complementary nucleotide triphosphate can nonetheless associate with the first unpaired deoxynucleotide monomer 2712 in the primer-associated template DNA strand, as shown in active-site representation 2604 of FIG. 26. It is the specific association of a complementary nucleotide triphosphate in the active site that elicits the signal-producing conformational changes in the DNA-polymerase shape-change sensor component. Thus, a primer-associated template DNA strand having a dideoxynucleotide monomer at the 3' end of the primer produces only a single voltage-signal curve indicative of the type of nucleotide triphosphate complementary to the first unpaired deoxynucleotide monomer 2712 in the primer-associated DNA template strand. In another implementation, a deoxynucleotide or ribonucleotide moiety is present at the 3' end of the primer. To prevent incorporation of a nucleotide triphosphate, no catalytic divalent metal cations are present, such as $Mg^{2+}$ or $Mn^{2+}$, for example, but rather non-catalytic divalent metals are used, such as $Ca^{2+}$ or $Sr^{2+}$, at a concentration of 0.5 mM to 10 mM.

FIG. 28 lists, in one example, different types of parameters that may be tuned in order to configure, calibrate, and tune operation of the second type of sequence-detection system. A first column 2802 includes parameters with initially fixed values that are generally adjustable only prior to initiation of sequence detection, although, in certain microfluidics and other implementations, it may be possible to dynamically alter the composition of the solutions in the solution-containing chambers of the cell as well as to dynamically adjust other of these parameters. A second column 2804 indicates parameters with values that can be adjusted during operation of the cell, but for which adjustment involves a significant lag time. A third column 2806 includes continuously tunable parameters that can be easily and straightforwardly adjusted during operation of the cell. This third group of parameters provide a basis for fine-ingrained tuning of the cell by control components during cell operation.

The initially-fixed parameters shown in column 2802 include the type of monovalent cations in the one or more monovalent-cation/chloride salts of the buffer used in the cell chambers, the concentrations of the monovalent-cation/chloride salts, the types and concentrations of the divalent-cation/chloride salts used in the cell chambers, the type of pH-buffering compound or compounds used in the cell chambers, the types and concentrations of other cell-chamber-buffer-solution constituents, including reducing agents such as dithiothreitol, the type of DNA polymerase, the type of porin, the type and structure of the tether used both to mechanically couple the DNA polymerase to the variable-resistance component and as a portion of the variable-resistance component, the type of primer-associated template, the primer-associated template concentration, the types and concentrations of the nucleotide triphosphates, the membrane or bilayer constituents, the types of the electrodes, the volume, shape, and dimension's of the cell chambers, and various other parameters of the cell. When different types of electrodes are used, different types of salts may be used as electrolytes.

Many of the initially-fixed parameters directly affect the length of the nucleotide-triphosphate-addition cycle discussed above with reference to FIG. 26. The length of the nucleotide-triphosphate-addition cycle is sensitive to the types and concentrations of nucleotide triphosphate, the type of polymerase, the pH of the buffer solution, and the concentrations of the various ionized salts. As one example, substituting $Na^+$, $Li^+$, $Rb^+$, $NH_4^+$ and/or $Cs^+$, for $K^+$ lengthens the nucleotide-triphosphate-addition cycle, increases open pore current, or increases the base discrimination, in certain cases. These cations can be introduced by adding salts of these cations with a variety of different inorganic and organic anions. The concentrations of other cations, anions, and other solution components may affect the length of the nucleotide-triphosphate-addition cycle and may therefore also be parameters that may be tuned in order to configure, calibrate, and tune operation of the second type of sequence-detection system. For each type of cell, values for the parameters shown in column 2802 can be evaluated by experimentation to tune cell operation for optimal or near-optimal operation, including tuning the length of the nucleotide-triphosphate-addition cycle to provide desirable sequencing speed while preserving a threshold level of sequence-determination accuracy.

Certain of parameters are adjustable during cell operation to significantly affect the length of the nucleotide-triphosphate-addition cycle as well as many other operational characteristics of the second type of sequence-detection system. These are the classic parameters that are varied and controlled to obtain deterministic and repeatable results for chemical reactions and systems as well as many other types of systems. These parameters include the temperature of the cell and its contents, the pressure, and the pH. Note that the adjustable parameters associated with lag times, like the initially-fixed parameters, can be evaluated by experimentation to select parameter values that provide desirable cell-operation characteristics.

The adjustable parameters include the magnitude of the voltage applied to the cell, the polarity of the applied voltage, and various instrumental parameters associated with operation of the current-to-voltage-converter circuitry and the analysis subsystem, provide opportunities for fine-ingrained control cell operation at microsecond, millisecond, and longer timescales. Use of certain of these parameters for controlling operation of the second type of sequence-detection system is described, below, in a series of control-flow diagrams.

Figure 29A:
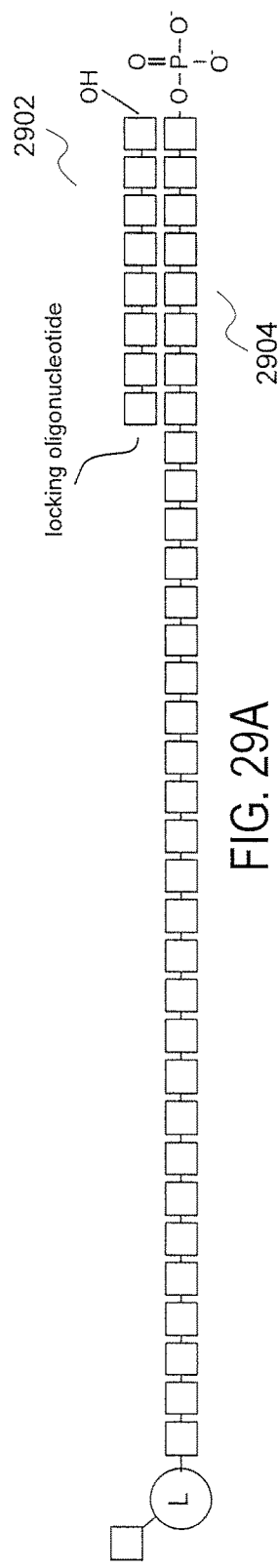
FIGS. 29A-29C illustrate, in one example, use of a locking oligonucleotide to securely hold the DNA-polymer tether within the porin channel.
Figure 29B:
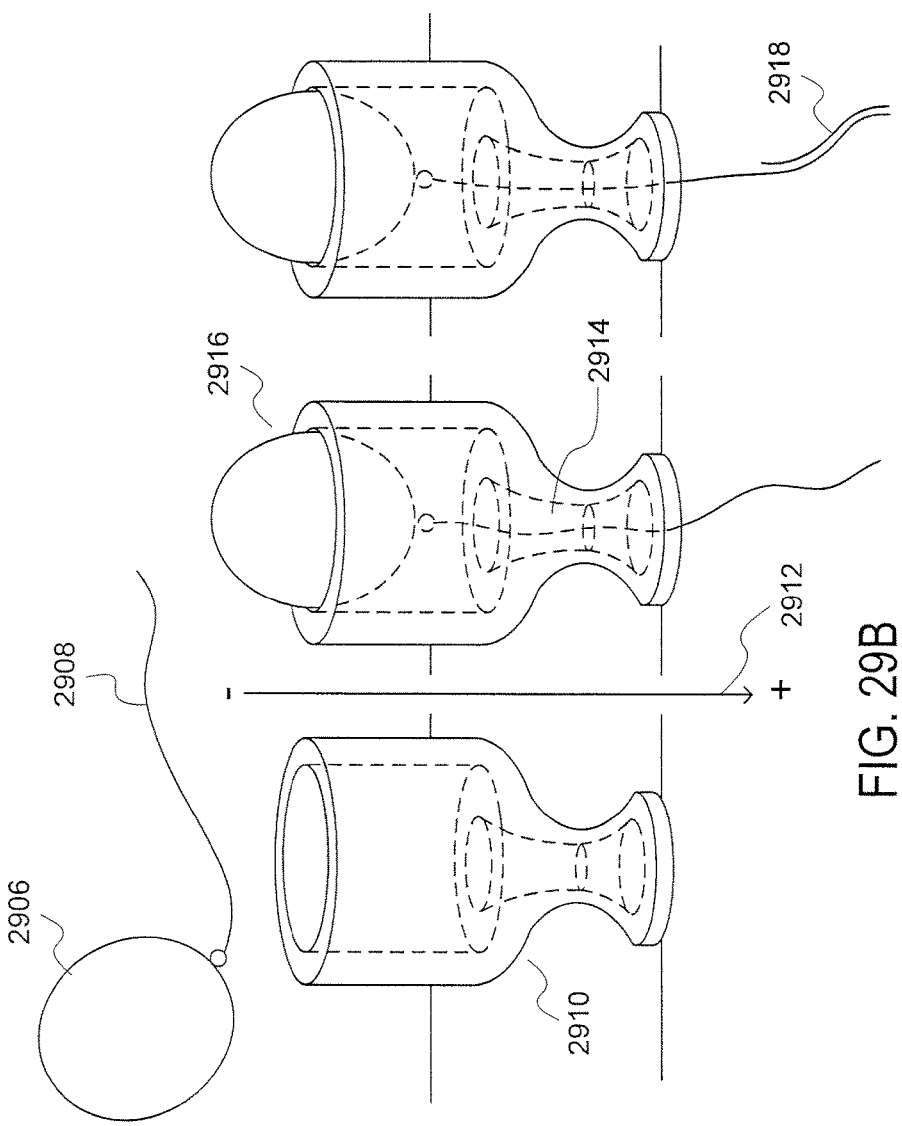
Figure 29C:
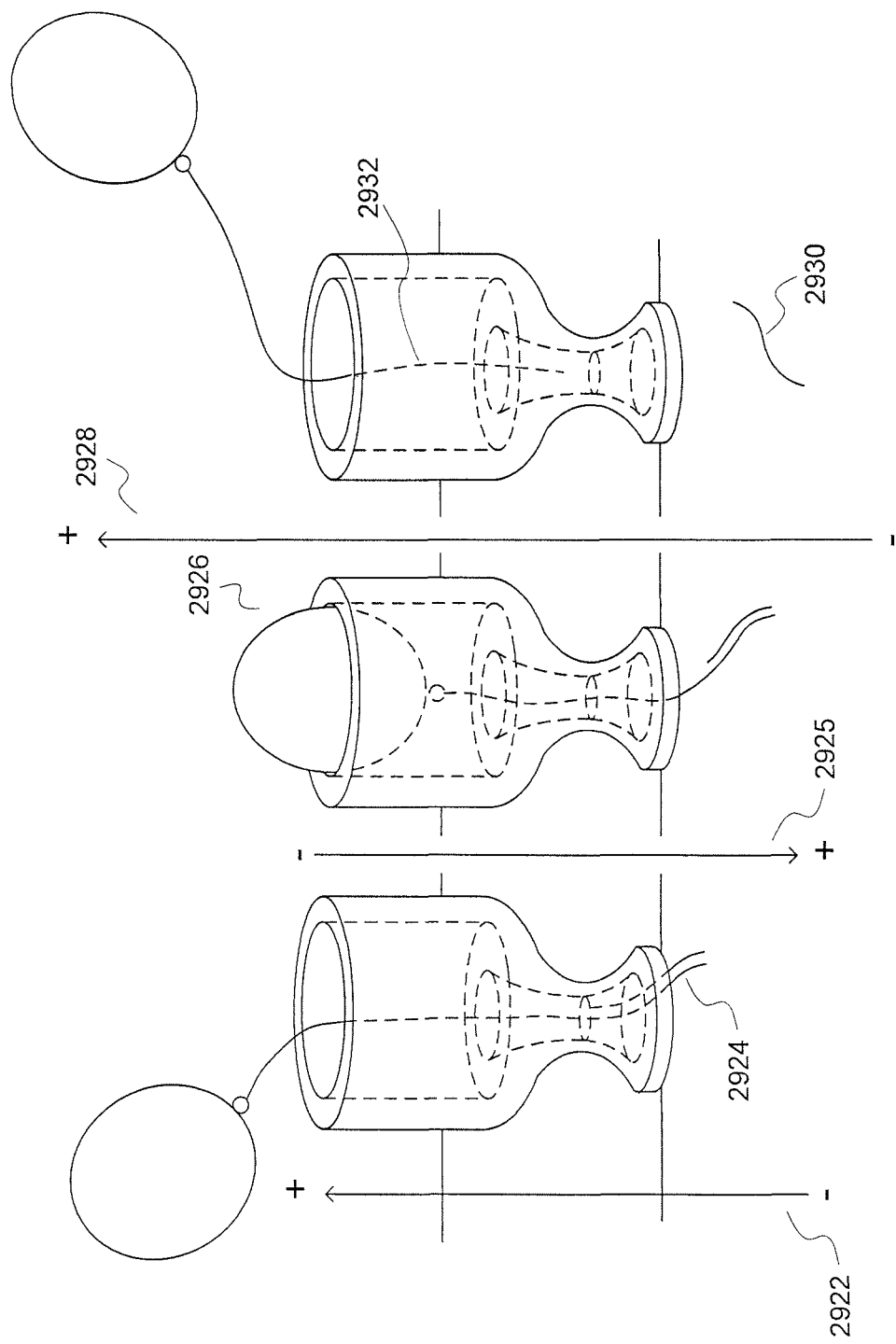

FIGS. 29A-29C illustrate, in one example, use of a locking oligonucleotide to securely hold the DNA-polymer tether within the porin channel. FIG. 29A illustrates a DNA—the polymer tether with a locking oligonucleotide using the same illustration conventions used previously in FIG. 24. As shown in FIG. 29A, the locking oligonucleotide 2902 has a deoxynucleotide-monomer sequence complementary to a portion of the deoxynucleotide-monomer sequence of the DNA-polymer tether 2904, and stably associates with the DNA-polymer tether via hydrogen bonding and base stacking. FIGS. 29B-C illustrate use of the locking oligonucleotide during cell operation. Initially, the DNA polymerase 2906 and the DNA-polymer tether 2908 are unassociated with the porin 2910. Application of a voltage drop across the cell 2912 results in threading of the DNA-polymer tether into and through the porin channel 2914 and seating of the DNA polymerase within the pore 2916. The locking oligonucleotide then associates with the portion of the DNA-polymer tether 2918 extending into the second solution-containing chamber of the cell. As shown in FIG. 29C, the locking oligonucleotide prevents the DNA-polymer tether from being pulled out of the porin channel 2920 when a reversed-polarity voltage 2922 is applied to the cell. As a result, restoring the original polarity of the applied voltage drop 2924 reseats the DNA polymerase within the porin 2926. However, application of a much larger reverse-magnitude voltage drop 2928 generates sufficient force to strip the locking oligonucleotide 2930 from the DNA-polymer tether 2932 and allow the DNA polymerase and DNA-polymer tether to fully dissociate from the port. In certain implementations, locking components other than locking oligonucleotides may be used. For example, a biotin moiety can be attached to tether and streptavidin can be used as the locking component. Other types of biopolymer locking components may also be used in alternative implementations.

FIGS. 30A-30H provide control-flow diagrams that illustrate one example of a sequencing process using the second type of sequence-detection system. The steps involve automated control activities carried out by control logic within control components of the sequence-detection system, including control components implemented within the analytic subsystem, but may also involve manual and semi-manual steps carried out by technicians.

Figure 30A:
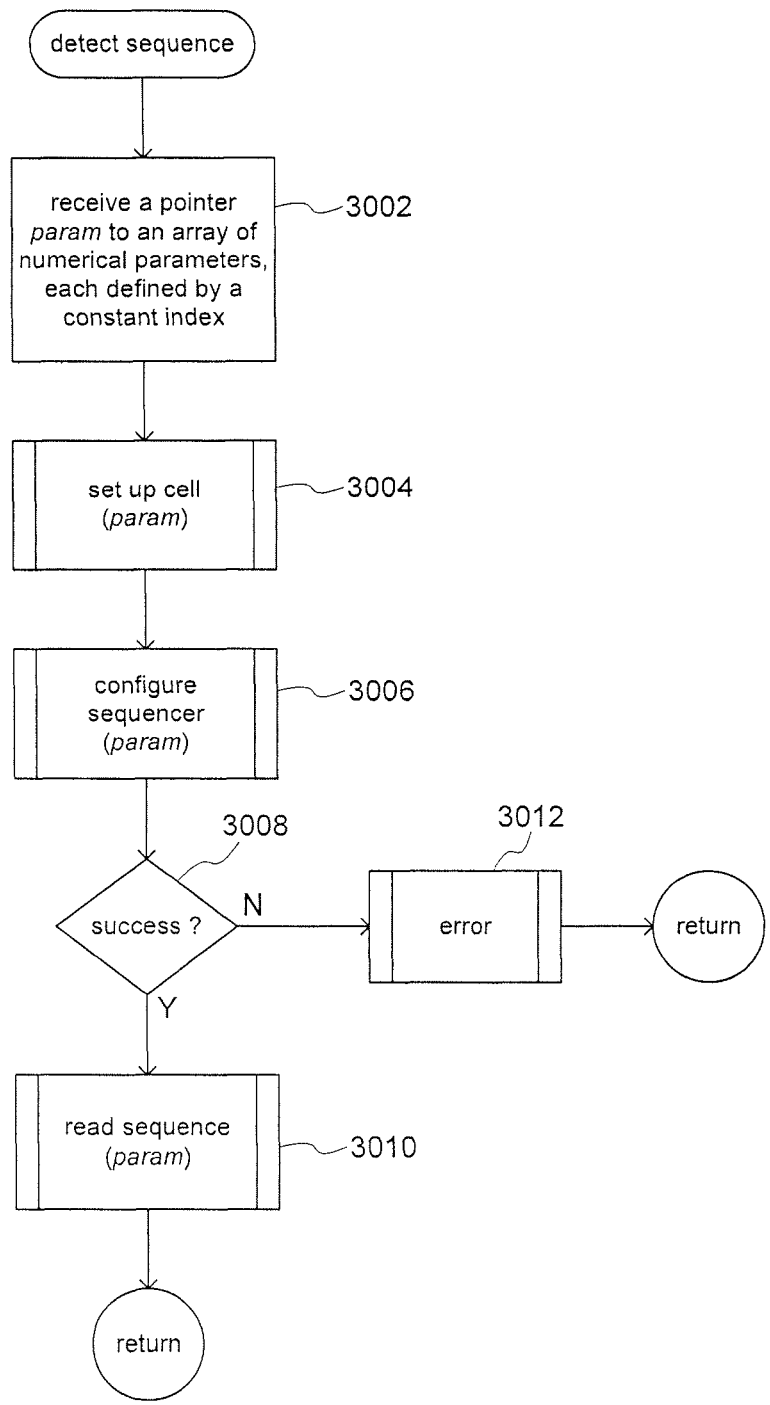
FIGS. 30A-30D provide control-flow diagrams that illustrate one example of control of one implementation of the second type of sequence-detection system.

FIG. 30A provides a control-flow diagram for a routine "detect sequence" that represents operation of the sequence-detection system to carry out one sequence-determination run during which the sequence-detection system is first configured and then operated to generate an output signal until one of several different termination conditions arises. In step 3002, the routine "detect sequence" receives a pointer param to an array of sequence-detector operational parameter values, each associated with a constant index. A particular parameter, such as a parameter containing a voltage magnitude for the voltage that is applied to the cell to generate an output signal containing sequence-identifying information, is denoted as param[ReadVolt], where ReadVolt is the index for the parameter in the array of parameters pointed to by the pointer param. These parameter values include values for the various fixed and adjustable parameters, discussed above with reference to FIG. 28. The parameter values also include several threshold values, further discussed below, and various timing parameters, also discussed below. In step 3004, a routine "set up cell" is called to configure the sequence-detector cell for the sequence-determination run. Cell configuration involves one or more of automated configuration steps, semi-automated configuration steps, and manual configuration steps. The text "(param)" indicates that the pointer param is passed to the routine as an argument. In step 3006, a routine "configure sequencer" is called to prepare the sequence-detector to begin generating an output signal. The routine "configure sequencer" is discussed, below, with reference to FIG. 30B. When the routine "configure sequencer" returns a success indication, as determined in step 3008, a routine "read sequence" is called, in step 3010, to generate an output signal from which the sequence of a biopolymer introduced into the cell is determined by the analysis subsystem of the sequence detector. Otherwise, when the routine "configure sequencer" returns a failure indication, an error-handling routine is called, in step 3012. This error-handling routine may report an inability to configure the sequence-detector for a sequence-determination run and may, in certain implementations, undertake automated ameliorative steps to address configuration failure and/or raise an alert to technicians and other personnel.

Figure 30B:
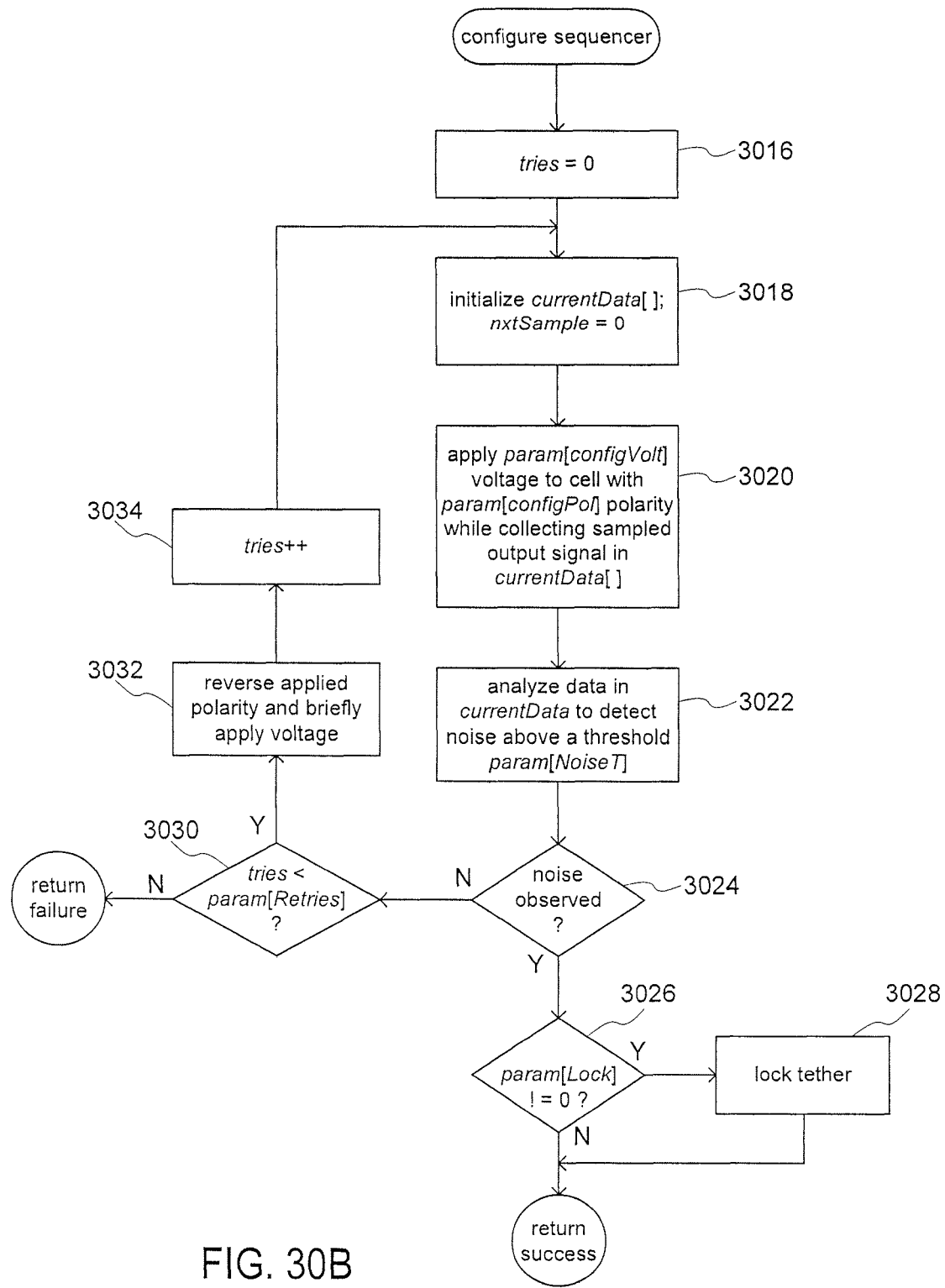

FIG. 30B provides a control-flow diagram for the routine "configure sequencer," called in step 3010 of FIG. 30A. The routine "configure sequencer" represents configuration of the sequence-detection system to carry out a sequence-determination run. In one implementation, configuration involves applying a voltage to the cell and analyzing the output voltage signal to look for periods of sequence-information-masking noise, discussed above with reference to FIG. 25. When sequence-information-masking noise is detected, the control logic infers that the DNA-polymer tether has been pulled through the porin channel and that the DNA-polymerase mechanical-change sensor component has been seated within the porin. In step 3016, the local variable tries is initialized to 0. In step 3018, a memory buffer represented by the array cuurentData is initialized along with an index nxtSample that indicates a next position within the memory buffer in which to store a signal sample. In Step 3020, a voltage with a magnitude indicated by the parameter value param[ConfigureVolt] and a polarity indicated by the parameter param[ConfigPol] is applied to the cell while sampled output signal is collected in the memory buffer currentData. In step 3022, the data in the memory buffer currentData is analyzed to determine whether noise above a threshold noise level indicated by the parameter value param[NoiseT] is observed in the sampled signal. When such noise has been observed, as determined in step 3024, the routine "configure sequencer" infers that the mechanical-change-sensor component is seated within the porin. When the parameter value param[Lock] is not equal to 0, as determined in step 3026, the tether is locked, in step 3028, as discussed above with reference to FIGS. 29A-29C. The routine "configures sequencer" then returns a success indication. When such noise is not observed, as determined in step 3024, and when the value of the local variable tries is less than the parameter value param[Retries], as determined in step 3030, a reversed-polarity voltage is applied to the cell briefly, in step 3032, and the value of the local variable tries is incremented, in step 3034, in preparation for again attempting to seat the DNA-polymerase mechanical-change-sensor component within the porin, beginning with step 3018. When the value stored in the local variable tries is greater than or equal to the value of the parameter param[Retries], as determined in step 3030, a failure indication is returned by the routine "configure sequencer."

Figure 30C:
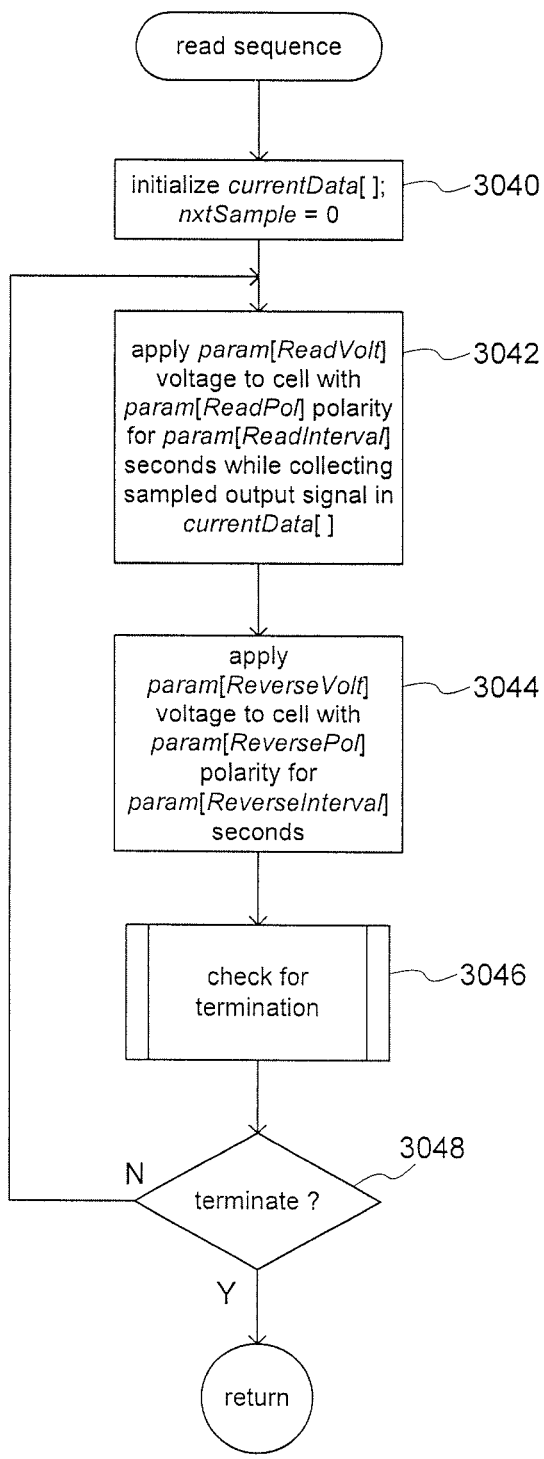

FIG. 30C provides a control-flow diagram for the routine "read sequence," called in step 3010 of FIG. 30A. The routine "read sequence" represents a sequence-determination run carried out by the sequence-detection system. The routine "read sequence" iterates through a series of voltage-application cycles until a termination condition arises. In step 3040, the memory buffer represented by the array cuurentData is initialized along with the index nxtSample that indicates a next position within the memory buffer in which to store a signal sample. In step 3042, the routine "read sequence" applies a voltage of magnitude param [ReadVolt] and polarity parameter [ReadPol] to the cell for a length of time indicated by the parameter param[ReadInterval] while collecting sampled output signal in the memory buffer currentData. In step 3044, the routine "read sequence" next applies a voltage of magnitude param[ReverseVolt] and polarity param[ReversePol] to the cell for a length of time indicated by the parameter param[ReverseInterval]. This reversed-polarity voltage application inhibits the occurrence of sequence-information-masking noise, as discussed above with reference to FIG. 25. In step 3046, the routine "read sequence" checks for a termination event by calling the routine "check for termination." When a termination event has occurred, as determined in step 3048, the routine "read sequence" returns. Otherwise, control flows back to step 3042 for another voltage-application cycle.

Figure 30D:
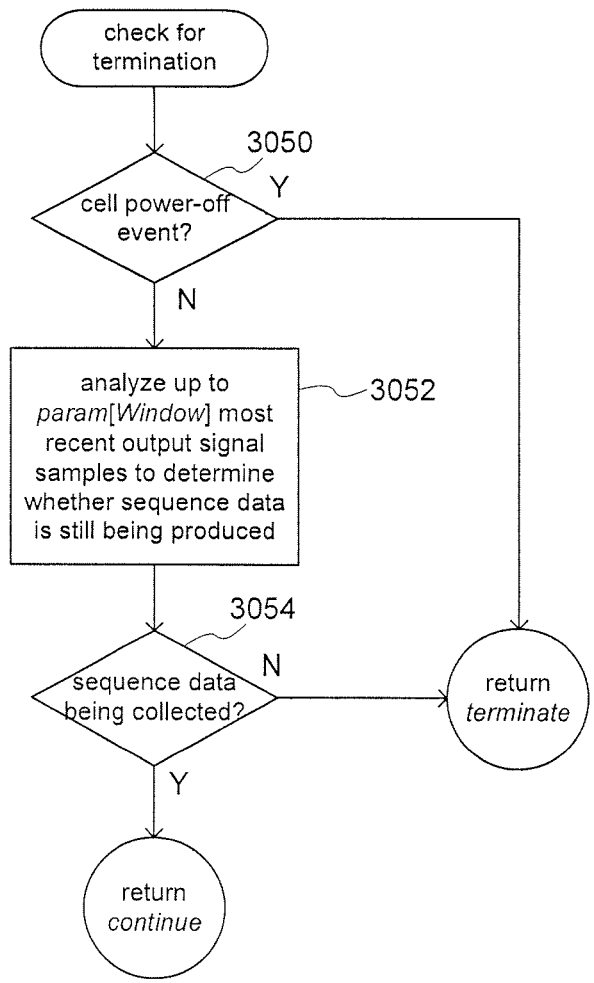

FIG. 30D provides a control-flow diagram for the routine "check for termination," called in step 3046 of FIG. 30D. In step 3050, the routine "check for termination" determines whether or not a power-off event has occurred, indicating that the cell is about to be powered down. If so, the routine "check for termination" returns a terminate indication. Otherwise, in step 3052, the routine "check for termination" analyzes the most recent output-signal samples stored in the memory buffer current data, where the most recent output-signal samples are indicated by the parameter value param [Window], which indicates a number of most recent output-signal samples in the memory buffer currentData to use to determine whether or not sequence data is still being produced by the cell at a rate above a threshold sequence-data rate. When the analysis shows that sequence data is still being collected at an acceptable rate, as determined in step 3054, the routine "check for termination" returns a continue indication. Otherwise, the routine "check for termination" recent returns a terminate indication. The rate of sequence data may fall due to clogging of the porin channel, electrode deterioration, and for many other reasons.

Although the present invention has been described in terms of particular embodiments, is not intended that the invention be limited to these embodiments. Modification within the spirit of the invention will be apparent to those skilled in the art. For example, any particular sequence-detection system may use a variety of different types of mechanical-change sensor components, mechanical couplers, variable-resistance components, and electrical-signal-generation components and circuitry. For example, any particular sequence-detection system may use a variety of different types of mechanical-change sensor components, mechanical couplers, variable-resistance components, and electrical-signal-generation components and circuitry. For example, the above-described second sequence-detection system may use different DNA polymerases and DNA-polymerase fragments, may use different porins, may use different types of mechanical couplers, including different types of polymers, and may employ cells of many different shapes, sizes, and configurations. Example polypeptide pores that may be used in place of MspA-porin include α-hemolysin, *Mycobacterium smegmatis* porin A, gramicidin A, maltoporin, OmpF, OmpC, PhoE, Tsx, F-pilus, SP1, mitochondrial porin (VDAC), Tom40, outer membrane phospholipase A, and *Neisseria* autotransporter lipoprotein (NalP). Example polymerases, or fragments thereof, that may be used in place of the above-discussed Klenow fragment include T7 DNA polymerase, eukaryotic mitochondrial DNA polymerase γ, *E. coli* DNA Pol I, *Thermus aquaticus* Pol I, *Bacillus stearothermophilus* Pol I, eukaryotic DNA polymerases α, δ, and ε, DNA polymerase ζ, T4 DNA polymerase, Phi29 DNA polymerase, RB69 bacteriophage DNA polymerase, *E. coli* DNA polymerase III alpha subunit, polymerases derived from the Euryarchaeota subdomain of Archaea, eukaryotic polymerases Pol β, Pol σ, Pol λ, and Pol μ, *S. cerevisiae* Pol4, Pol η, Pol iota, Pol kappa, *E. coli* Pol IV (DINB), *E. coli* Pol V (UmuD'2C), retrovirus reverse transcriptases and eukaryotic telomerases, viral RNA polymerases such as T7 RNA polymerase, Eukaryotic RNA polymerases such as RNA polymerase I, RNA polymerase II, RNA polymerase III, RNA polymerase IV, RNA polymerase V, and Archaea RNA polymerase. Example alternative tethers include synthetic polymers such as PEG (polyethylene glycol), PPG (polypropylene glycol), PVA (polyvinyl alcohol), and PE (polyethylene) Additionally, DNA, RNA, PNA or LNA labels, morpholinos, or enantiomeric DNA, for example. Additionally, in one illustrative implementation, isoG and isoC bases can be on the tether. Various different values derived from the output voltage signal can be employed as different dimensions for uniquely identifying the types of objects or entities in target sequences. The average voltage-signal magnitude, the variance, and the standard deviation computed from the voltage signals are only a few examples of the many different types of derived values that can be used for object or entity type identification. Many different types of modified deoxynucleotide triphosphates can be used for copy-strand extension in addition to 7-deaza deoxyadenosine triphosphate. Copy-strand elongation is only used to determine the template-strand sequence, and thus the chemical composition of the copy strand produced during sequence determination is irrelevant to successful operation of the second sequence-detection system. All combinations of the discussed concepts, components, and methods have been considered and comprehended.

It should be appreciated that all combinations of the foregoing concepts and additional concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The invention claimed is:

1. A sequence-detection system comprising:
   a mechanical-change sensor that exhibits one or more mechanical changes when specifically interacting with entities within a target, each entity having a type;
   a mechanical-change-to-signal transducer that transduces the one or more mechanical changes into a signal;
   an analysis subsystem that determines a sequence of entity types within the target using the signal; and
   a control subsystem that
   is configured to initialize the sequence-detection system in accordance with one or more operational parameters,
   initializes the sequence-detection system in accordance with one or more operational parameters,
   is configured to control the sequence-detection system to generate, collect samples of, and analyze the signal to determine the sequence of entity types within the target, and
   controls the sequence-detection system to generate, collect samples of, and analyze the signal to determine the sequence of entity types within the target,
   wherein the target is a primer-associated nucleic-acid template polymer;
   wherein the entities are nucleotide monomers;
   wherein the mechanical-change sensor is a nucleic-acid-polymerase mechanical-change sensor contained within a first solution-containing chamber; and
   wherein the mechanical-change-to-signal transducer further comprises
   a variable resistor that regulates flow of an electrical current through a porin channel that provides fluid communication between the first solution-containing chamber and a second solution-containing chamber,
   a mechanical coupler that couples the nucleic-acid-polymerase mechanical-change sensor to the variable resistor, and
   a current-to-voltage converter that outputs a voltage signal that varies in correspondence with a rate of flow of the electrical current through the porin channel,
   wherein the one or more operational parameters include:
      a voltage magnitude of a read voltage applied across the porin channel and a polarity of the read voltage;
      a voltage magnitude of a noise-inhibition voltage applied across the porin channel and a polarity of the noise-inhibition voltage; and
      a voltage magnitude of a configuration voltage applied across the porin channel and a polarity of the configuration voltage.

2. The sequence-detection system of claim 1
   wherein the polarity of the noise-inhibition voltage is opposite from the polarity of the read voltage; and
   wherein the polarity of the noise-inhibition voltage is opposite from the polarity of the configuration voltage.

3. The sequence-detection system of claim 1 wherein the control subsystem configures the sequence-detection system by:
   applying the configuration voltage across the porin channel with the configuration polarity to seat the nucleic-acid-polymerase mechanical-change sensor within the porin.

4. The sequence-detection system of claim 3 wherein, following configuration of the sequence-detection system, the control subsystem adjusts the read voltage magnitude to position a reporter region of a nucleic-acid-polymer tether at a reference displacement.

5. The sequence-detection system of claim 1 wherein, following configuration of the sequence-detection system, the control subsystem controls the sequence-detection system to generate, collect samples of, and analyze the signal to determine the sequence of entity types within the target by:
   iteratively
   applying the read voltage across the porin channel with the polarity of the read voltage for a first time period, during which the voltage output signal is sampled, stored in a memory, and analyzed by the analysis subsystem, and
   applying the noise-inhibition voltage across the porin channel with the polarity of the noise-inhibition voltage for a second time period
   until a termination condition occurs.

6. The sequence-detection system of claim 5 wherein lengths of the first and second time periods are specified by operational parameters.

7. The sequence-detection system of claim 5 wherein termination conditions include:
   a power-off event; and
   a decrease in a rate of sequence-information generation below a threshold level by the sequence-detection system.

8. The sequence-detection system of claim 1 wherein the operational parameters include:
   temperature;
   pH of solutions in the first and second solution-containing chambers; and
   contents of the solutions in the first and second solution-containing chambers.

9. The sequence-detection system of claim 8 wherein the operational parameter related to the contents of the solutions in the first and second solution-containing chambers encompasses one or more of:
   one or more types of ionized salts in the solutions;
   concentrations of the one or more types of ionized salts in the solutions;
   one or more types of nucleotide polyphosphates in the solution in the first solution-containing chamber;
   concentrations of the one or more types of nucleotide polyphosphates in the solution in the first solution-containing chamber;
   one or more types of primer-associated nucleic-acid template polymers in the solution in the first solution-containing chamber;
   concentrations of the one or more types of primer-associated nucleic-acid template polymers in the solution in the first solution-containing chamber; and
   a type and structure of a nucleic-acid-polymer tether.

10. The sequence-detection system of claim 8 wherein the operational parameter related to the contents of the solution in the solution in the first solution-containing chamber is adjusted to control the rate of sequential specific interaction of the mechanical-change sensor with entities within the target.

11. The sequence-detection system of claim 8 wherein a primer with a 3' dideoxynucleotide monomer is employed to constrain the sequence-detection system to specifically interact with a single entity.

12. The sequence-detection system of claim 1 wherein a signal response of the sequence-detection system is configured by selecting a reporter region with a nucleotide-monomer sequence corresponding to the signal response.

* * * * *

UNITED STATES PATENT AND TRADEMARK OFFICE
CERTIFICATE OF CORRECTION

PATENT NO. : 11,976,322 B2  
APPLICATION NO. : 16/623634  
DATED : May 7, 2024  
INVENTOR(S) : Jeffrey G. Mandell et al.

Page 1 of 1

It is certified that error appears in the above-identified patent and that said Letters Patent is hereby corrected as shown below:

On the Title Page

Column 1, "TUNING AND CALIBRATION FEATURES OF SEQUENCE-DETECTION SYSTEM," should be --TUNING AND CALIBRATION FEATURES OF A SEQUENCE-DETECTION SYSTEM--

In the Specification

At Column 1, "TUNING AND CALIBRATION FEATURES OF SEQUENCE-DETECTION SYSTEM," should be --TUNING AND CALIBRATION FEATURES OF A SEQUENCE-DETECTION SYSTEM--

In the Claims

At Column 28, Lines 53 and 54, "the contents of the solution in the solution in the first solution-containing chamber is," should be --the contents of the solutions in the first and second solution-containing chambers is--

Signed and Sealed this  
Tenth Day of December, 2024

Katherine Kelly Vidal  
*Director of the United States Patent and Trademark Office*